US006872721B2

(12) United States Patent
Orme et al.

(10) Patent No.: US 6,872,721 B2
(45) Date of Patent: Mar. 29, 2005

(54) DERIVATIVES OF 2,3,6,7,12,12A-HEXAHYDROPYRAZINO-[1',2':1,6]PYRIDO[3,4B]-INDOLE-1,4-DIONE

(75) Inventors: Mark W. Orme, Seattle, WA (US); Jason Scott Sawyer, Indianapolis, IN (US); Alain Claude-Marie Daugan, Les Ulis (FR)

(73) Assignee: Lilly ICOS LLC, Wilmington, DE (US)

( * ) Notice: Subject to any disclaimer, the term of this patent is extended or adjusted under 35 U.S.C. 154(b) by 67 days.

(21) Appl. No.: 10/297,245

(22) PCT Filed: May 15, 2001

(86) PCT No.: PCT/US01/15936

§ 371 (c)(1),
(2), (4) Date: Dec. 3, 2002

(87) PCT Pub. No.: WO01/94345

PCT Pub. Date: Dec. 13, 2001

(65) Prior Publication Data

US 2003/0225092 A1 Dec. 4, 2003

Related U.S. Application Data

(60) Provisional application No. 60/210,137, filed on Jun. 7, 2000.

(51) Int. Cl.[7] .................. C07D 487/14; A61K 31/4985; A61P 9/12; A61P 9/10; A61P 37/08
(52) U.S. Cl. ........................ 514/250; 544/342; 544/343
(58) Field of Search ................................. 544/342, 343; 514/250

(56) References Cited

U.S. PATENT DOCUMENTS 5,859,006 A    1/1999  Daugan

FOREIGN PATENT DOCUMENTS

WO    WO 97/03675    2/1997

OTHER PUBLICATIONS

Chalmers (TiPS vol. 17, pp. 166–172 Apr. 1996).*

* cited by examiner

*Primary Examiner*—Mark L. Berch
*Assistant Examiner*—Kahsay Habte
(74) *Attorney, Agent, or Firm*—Marshall, Gerstein & Borun LLP

(57) ABSTRACT

Compounds of the general structural formula (I) and use of the compounds and salts and solvates thereof, as therapeutic agents.

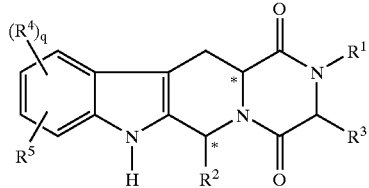

21 Claims, No Drawings

DERIVATIVES OF 2,3,6,7,12,12A-HEXAHYDROPYRAZINO-[1',2':1,6]PYRIDO [3,4B]-INDOLE-1,4-DIONE

CROSS REFERENCE TO RELATED APPLICATION

This is the U.S. national phase application of International Application No. PCT/US01/15936, filed May 15, 2001, which claims the benefit of provisional patent application Ser. No. 60/210,137, filed Jun. 7, 2000.

FIELD AND BACKGROUND OF THE INVENTION

This invention relates to a series of compounds, to methods of preparing the compounds, to pharmaceutical compositions containing the compounds, and to their use as therapeutic agents. In particular, the PRESENT invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

DETAILED DESCRIPTION OF THE INVENTION

The present invention is directed to compounds having the general structural formula (I):

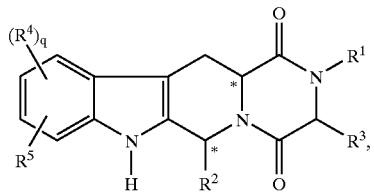

(I)

wherein $R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, hetero$C_{3-8}$cycloalkyl, $C_{3-8}$cycloalkyl$C_{1-3}$alkyl, aryl$C_{1-3}$-alkyl, and heteroaryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

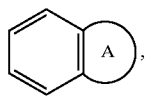

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is selected from the group consisting of hydrogen and $C_{1-6}$alkyl, or $R^1$ and $R^3$ together represent a 3- or 4-membered alkyl or alkenyl chain component of a 5- or 6-membered ring;

$R^4$, independently, is selected from the group consisting of aryl,

Het, $C_{3-8}$cycloalkyl, $YC_{3-8}$cycloalkyl (wherein Y is oxygen, sulfur, or $NR^a$), $C(=O)R^a$, $OC(=O)R^a$, $C(=O)OR^a$, $C_{1-4}$alkyleneNR$^a$R$^b$, $C_{1-4}$alkyleneHet, $C_{1-4}$alkyleneC(=O)OR$^a$, $C(=O)NR^aSO_2R^c$, $C(=O)C_{1-4}$alkyleneHet, $C(=O)NR^aR^b$, $C(=O)NR^aR^c$, $C(=O)NR^aC_{1-4}$alkyleneOR$^b$, $C(=O)NR^aC_{1-4}$alkyleneHet, $OR^a$, $OC_{1-4}$alkyleneC(=O)OR$^a$, $OC_{2-4}$alkyleneNR$^a$R$^b$, $OC_{1-4}$alkyleneHet, $OC_{2-4}$alkyleneOR$^a$, $OC_{1-4}$alkyleneNR$^a$C(=O)OR$^b$, $NR^aR^b$, $NR^aC_{1-4}$alkyleneNR$^a$R$^b$, $NR^aC(=O)R^b$, $NR^aC(=O)NR^aR^b$, $N(SO_2C_{1-4}$alkyl$)_2$, $NR^a(SO_2C_{1-4}$alkyl$)$, nitro ($NO_2$), trifluoromethyl, trifluoromethoxy, cyano (CN), $SO_2NR^aR^b$, $SO_2R^a$, $SOR^a$, $SR^a$, and $OSO_2CF_3$;

$R^5$ is selected from the group consisting of hydrogen, halogen, and $C_{1-6}$alkyl;

or $R^4$ and $R^5$ are taken together with the carbon atoms to which they are attached to form a 5-, 6-, or 7-membered ring, saturated or partially or fully unsaturated, optionally substituted and optionally containing one or two heteroatoms selected from the group consisting of oxygen, sulfur, and nitrogen;

$R^a$ is selected from the group consisting of hydrogen, $C_{1-6}$alkyl, $C_{3-8}$cycloalkyl, aryl, aryl$C_{1-3}$alkyl, $C_{1-3}$alkylenearyl, and Het;

$R^b$ is selected from the group consisting of hydrogen, $C_{1-6}$alkyl, aryl, aryl$C_{1-3}$alkyl, $C_{1-3}$alkylenearyl, and Het;

$R^c$ is phenyl or $C_{4-6}$cycloalkyl, either optionally substituted with one or more substituents selected from the group consisting of halo, $C(=O)OR^a$, and $OR^a$;

Het is a 5- or 6-membered heterocyclic group, saturated or partially or fully unsaturated, containing at least one heteroatom selected from the group consisting of oxygen, nitrogen, and sulfur, and optionally substituted with $C_{1-4}$alkyl or $C(=O)OR^b$;

q is 1, 2, or 3; and pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or deca-hydronaphthyl. The term "cycloalkyl" is defined as a cyclic $C_3$–$C_8$ hydrocarbon group, e.g., cyclopropyl, cyclobutyl, cyclohexyl, and cyclopentyl.

"Heterocycloalkyl" is similarly defined as a ring containing three to eight atoms, with one to three atoms selected from the group consisting of oxygen, nitrogen, and sulfur, with the remaining atoms being carbon.

The terms "alkenyl" and "alkynyl" are defined identically as "alkyl," except for containing a carbon-carbon double bond or carbon-carbon triple bond, respectively.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetra-hydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrinidinyl, thiazolyl, and thiadiazolyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxy" is defined as —OH.

The term "alkoxy" is defined as —OR, wherein R is alkyl.

The term "hydroxyalkyl" is defined as a hydroxy group appended to an alkyl group.

The term "amino" is defined as —$NH_2$, and the term "alkylamino" is defined as —$NR_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—$SO_2$, wherein R is alkyl.

The term "alkylsulfonyl" is defined as R—$SO_3$, wherein R is alkyl.

The term "nitro" is defined as —$NO_2$.

The term "trifluoromethyl" is defined as —$CF_3$.

The term "trifluoromethoxy" is defined as —$OCF_3$.

The term "cyano" is defined as —CN.

In a preferred embodiment, $R^1$ is selected from the group consisting of hydrogen, $C_{1-6}$alkyl, halo$C_{1-6}$alkyl, $C_{3-8}$cycloalkyl, $C_{3-8}$cycloalkyl$C_{1-3}$alkyl, aryl$C_{2-3}$alkyl, and heteroaryl$C_{2-3}$alkyl.

In a preferred embodiment, $R^2$ is the optionally substituted bicyclic ring system

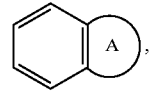

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

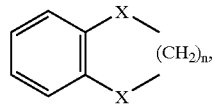

wherein n is an integer 1 or 2, and X, independently, are $C(R^a)_2$, O, S, or $NR^a$. The bicyclic ring comprising the $R^2$ substituent typically is attached to the rest of the molecule by a phenyl ring carbon atom.

In a preferred group of compounds of formula (I), $R^2$ is represented by an optionally substituted bicyclic ring

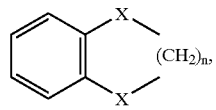

wherein n is 1 or 2, and X, independently, are $CH_2$ or O. Especially preferred $R^2$ substituents include

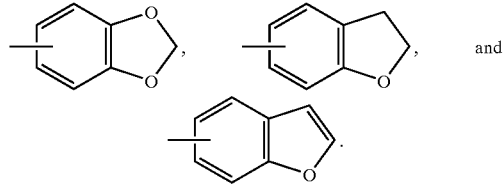

Within this particular group of compounds, nonlimiting examples of substituents for the bicyclic ring include halogen (e.g., chlorine), $C_{1-3}$alkyl (e.g., methyl, ethyl, or i-propyl), $OR^a$ (e.g., methoxy, ethoxy, or hydroxy), $CO_2R^a$, halomethyl or halomethoxy (e.g., trifluoromethyl or trifluoromethoxy), cyano, nitro, and $NR^aR^b$.

In another preferred embodiment, $R^4$ is selected from the group consisting of aryl, Het, $OR^a$, C(=O)$OR^a$, $C_{1-4}$alkyleneNR$^a$R$^b$, OC(=O)$R^a$, C(=O)$R^a$, $NR^aR^b$, $C_{3-8}$cycloalkyl, $C_{3-8}$cycloalkylY, C(=O)NR$^a$R$^b$, $CF_3$, $OCF_3$, CN, $SO_2$NR$^a$R$^b$, OC$_{2-4}$alkyleneNR$^a$R$^b$, and C(=O) NR$^a$R$^c$, or $R^4$ and $R^5$ are taken together with the carbon atoms to which they are attached to form a 5- or 6-membered ring, saturated or partially or fully saturated, optionally substituted and optionally containing one or two heteroatoms.

An especially preferred subclass of compounds within the general scope of formula (I) is represented by compounds of formula (II)

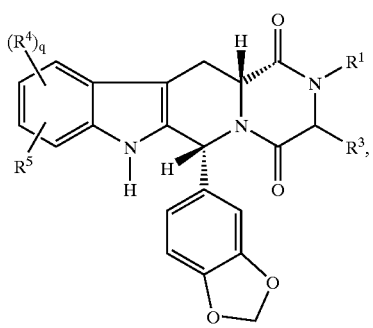

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder, also termed female sexual arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female sexual arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and sexual arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female sexual arousal disorder, they also can be used for the treatment of other disease states. A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and intervals can be adjusted individually to provide plasma levels of the active moiety which are sufficient to maintain therapeutic effects.

The amount of composition administered is dependent on the subject being treated, the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances wherein higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds readily can be formulated by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected-parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^1$, $R^2$, $R^3$, $R^4$, and $R^5$ are as defined in structural formula (I) above. In particular, Daugan U.S. Pat. No. 5,859,006, incorporated herein by reference, discloses preparation of a compound of structural formula (III).

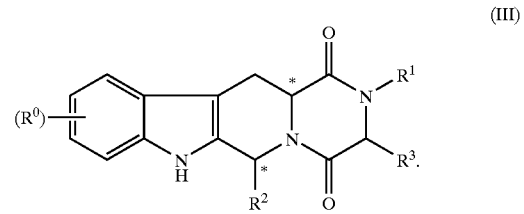

(III)

Daugan U.S. Pat. No. 5,859,006 teaches the preparation of the compound of structural formula (III), wherein $R^0$ is H, beginning with a tryptophan ester having the structural formula (IV):

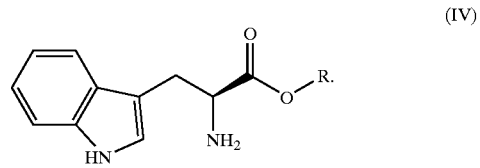

(IV)

D-Tryptophan ester

The compounds of structural formula (I) can be prepared in an analogous manner as a compound of structural formula (III) using an appropriately substituted tryptophan ester of structural formula (V):

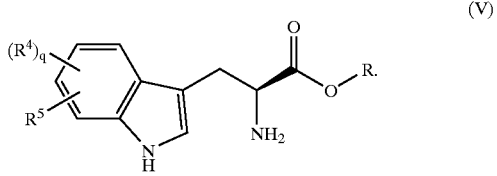

Many substituted tryptophan esters of structural formula (V) are commercially available, and, if necessary, can be converted to other substituted esters. Substituted tryptophan esters also can be prepared, for example, from substituted indoles, as set forth in S. Wagaw et al., *J. Amer. Chem. Soc.*, 21, p. 10251 (1999) and M. P. Moyer et al., *J. Org. Chem.*, 51, p. 5106 (1986). These substituted tryptophan esters can be used in the synthetic methods disclosed in Daugan U.S. Pat. No. 5,859,006 to provide compositions of structural formula (I).

It should be understood that protecting groups can be utilized in accordance with general principles of organic synthetic chemistry to provide compounds of structural formula (I). Protecting compounds and protecting groups, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

In addition, compounds of formula (I) can be converted to other compounds of formula (I). Thus, for example, a particular $R^4$ substituent can be interconverted to prepare another suitably substituted compound of formula (I). Examples of appropriate interconversions include, but are not limited to, nitro to amino, $OR^a$ to hydroxy by suitable means (e.g., using a reducing agent such as $SnCl_2$ or a palladium catalyst, such as palladium-on-carbon), or amino to substituted amino, such as acylamino or sulphonylamino, using standard acylating or sulfonylating conditions. In cases wherein $R^1$ represents a substituted bicyclic system, suitable interconversion can involve removal of a substituent, such as by treatment with a palladium catalyst whereby, for example, a benzyl substituent is removed from a suitable bicyclic system.

Compounds of formula (I) can be prepared by the method above as individual stereoisomers from the appropriate stereoisomer of formula (IV) or as a racemic mixture from the appropriate racemic compound of formula (IV). Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following abbreviations are used hereafter in the accompanying examples: rt (room temperature), min (minute), h (hour), g (gram), mmol (millimole), m.p. (melting point), eq (equivalents), aq (aqueous), L (liter), mL (milliliter), μL (microliter), DMSO (dimethyl sulfoxide), $CH_2Cl_2$ (dichloromethane), IPA (isopropyl alcohol), TFA (trifluoroacetic acid), NaOH (sodium hydroxide), TsOH (p-toluenesulfonic acid), Me (methyl), Et (ethyl), EtOH (ethanol), MeOH (methanol), DMF (dimethylformamide), $Et_3N$ (triethylamine), $MeNH_2$ (methylamine), HOAC (acetic acid), $Ac_2O$ (acetic anhydride), Ac ($C(=O)CH_3$), and THF (tetrahydrofuran).

PREPARATION OF EXAMPLE 1

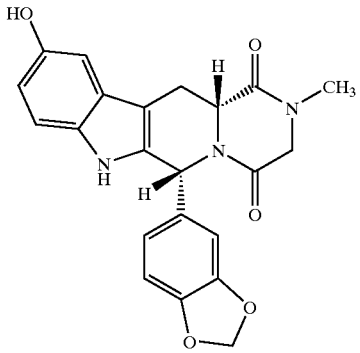

EXAMPLE 1

Example 1 was prepared from 5-hydroxy-DL-tryptophan as depicted in the following synthetic scheme. 5-Hydroxy-DL-tryptophan is a commercially available compound from Aldrich Chemical Co., Milwaukee, Wis.

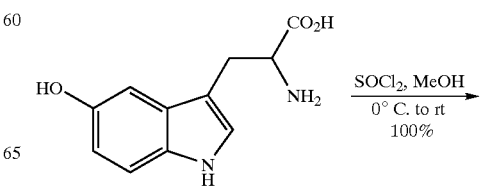

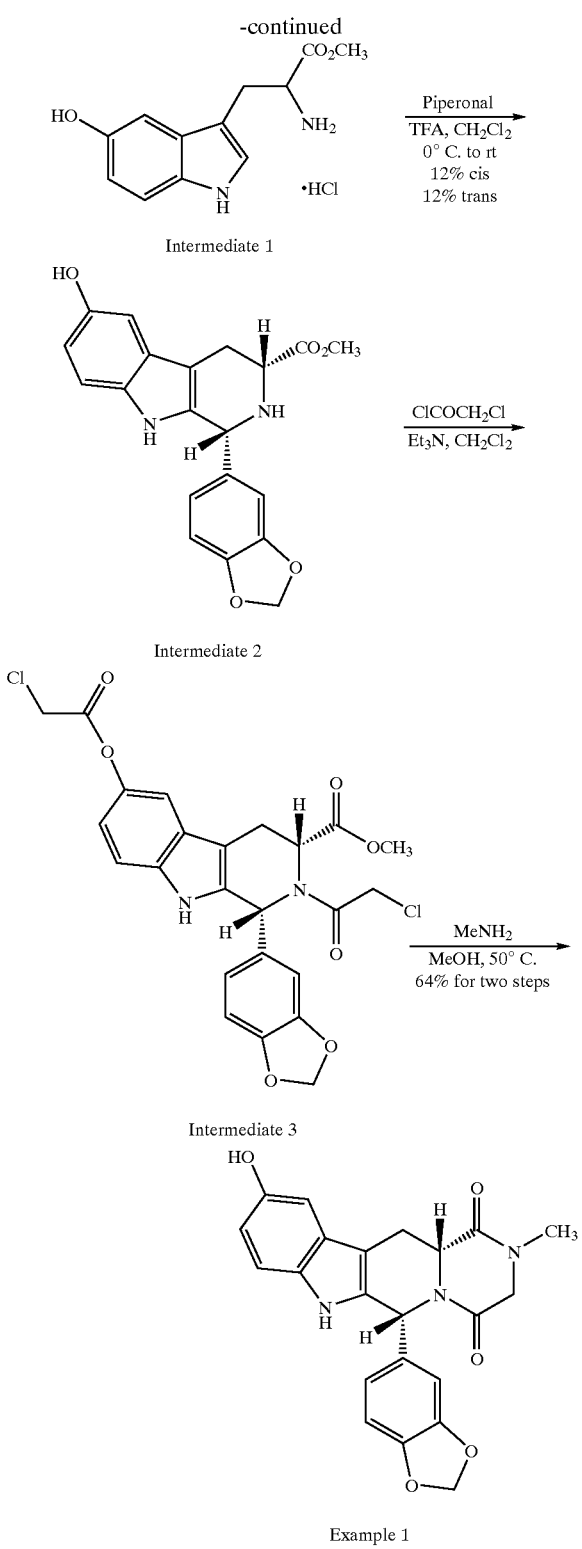

Intermediate 1
Preparation of 5-hydroxy-DL-tryptophan methyl ester hydrochloride Thionyl chloride (2.14 mL, 29.4 mmol) was added dropwise to a slurry of 5-hydroxy-DL-tryptophan (3.8 g, 17.3 mmol) in anhydrous methanol (40 mL) at 0° C. under a nitrogen blanket. The resulting mixture was warmed slowly to room temperature and stirred for 17 hours. Then the solvent was removed under reduced pressure to provide 5-hydroxy-DL-tryptophan methyl ester hydrochloride (Intermediate 1) as a light brown foam (5.0 g, 100%): $^1$H NMR (300 MHz, DMSO-$d_6$): δ 10.78 (bs, 1H), 8.62–8.25 (m, 3H), 7.18–7.11 (m, 2H), 6.79 (s, 1H), 6.67–6.61 (m, 1H), 4.18 (m, 1H), 3.69 (s, 3H), 3.25–3.12 (m, 2H).

Intermediate 2
Preparation of a cis-β-Carboline

A mixture of Intermediate 1 (2.7 g, 10 mmol) and piperonal (1.8 g, 12 mmol) in IPA (27 mL) was heated at reflux under a nitrogen blanket for 8 hours, during which time a precipitate formed (after about 4 hours). The resulting slurry was cooled to room temperature, vacuum filtered, and the solid was washed with IPA (2×5 mL). The filtrate solvent was removed under reduced pressure, then the residue was diluted with ethyl acetate (60 mL) and neutralized with saturated sodium bicarbonate (NaHCO$_3$) solution (20 mL). The basic aqueous layer was extracted with ethyl acetate, then the combined organic extracts were concentrated under reduced pressure to provide a yellow solid residue. The residue was purified by column chromatography, eluting with methylene chloride/ethyl acetate (4:1), to provide Intermediate 2 as a yellow solid (420 mg, 12%): TLC R$_f$ (4:1 methylene chloride/ethyl acetate)=0.55; $^1$H NMR (300 MHz, CDCl$_3$): δ 7.31 (bs, 1H), 7.07 (d, J=8.5 Hz, 1H), 6.92–6.68 (m, 5H), 5.95 (s, 2H), 5.14 (s, 1H), 3.97–3.91 (m, 1H), 3.81 (s, 3H), 3.19–3.08 (m, 1H), 3.00–2.88 (m 1H). The trans carboline also was obtained as a yellow solid, but was not characterized (420 mg, 12%): TLC R$_f$ (4:1 methylene chloride/ethyl acetate)=0.20.

Intermediate 3
Preparation of (+/−)-cis-2-chloroacetyl-β-carboline

Chloroacetyl chloride (0.36 mL, 4.52 mmol) was added dropwise to a mixture of Intermediate 2 (500 mg, 1.28 mmol) and triethylamine (0.63 mL, 4.54 mmol) in methylene chloride (20 μL) at 0° C. under a nitrogen blanket, and the resulting mixture was stirred at 5° C. for 2.5 hours. The resulting brown solution was diluted with methylene chloride (40 mL) and washed successively with saturated NaHCO$_3$ (15 mL) and brine (10 mL). The organic layer was dried over sodium sulfate (Na$_2$SO$_4$), then the solvent was removed under reduced pressure to provide Intermediate 3 as a thick yellow oil (0.95 g), which was used without purification: TLC R$_f$ (4:1 methylene chloride/ethyl acetate)=0.92.

EXAMPLE 1
Preparation of (+/−, cis)-6-Benzo[1,3]dioxol-5-yl-10-hydroxy-2-methyl-2,3,6,7,12,12a-hexahydropyrazino[1',2':1,6)pyrido[3,4-b]indole-1,4-dione A mixture of crude Intermediate 3 (0.95 g), methylamine (4.5 mL, 2.0M in THF, 9 mmol), and methanol (8 mL) was heated at 50° C. under a nitrogen blanket for 5 hours, after which the resulting mixture was heated for 17 hours at 40° C. The resulting orange slurry was cooled to room temperature, then the precipitate was collected by vacuum filtration. The solid was washed with methanol (5×2 mL), slurried in diethyl ether for 5 hours, then the solid was collected by vacuum filtration. The solid next was dried in a vacuum oven at 70° C. for 24 hours to provide the compound of Example 1 as a white powder (0.33 g, 64% for two steps). The desired cis isomer was confirmed by an NOE difference experiment (1.0% enhancement): mp 322–328° C.; TLC R$_f$ (4:1:0.4 methylene chloride/ethyl acetate/methanol)=0.55; $^1$H NMR (300 MHz, DMSO-$d_6$): δ 10.70 (s, 1H), 8.67 (s, 1H), 7.08 (d, J=8.6 Hz, 1H), 6.85–6.75 (m, 3H), 6.60–6.55 (m, 1H), 6.09 (s, 1H), 5.93 (s, 2H), 4.42–4.33 (m, 1H), 4.18 (d, J=17.0 Hz, 1H), 3.93 (d, J=17.0

Hz, 1H), 3.45–3.32 (m, 1H), 3.00–2.88 (m, 4H); $^{13}$C NMR (75 MHz, DMSO-d$_6$): δ 166.8, 166.6, 150.6, 146.9, 145.9, 137.0, 134.2, 130.6, 136.4, 119.1, 111.6, 111.2, 107.9, 106.8, 103.9, 102.1, 100.8, 55.4, 55.1, 51.4, 32.8, 23.0 ppm; CI MS (methane) m/z 406 [M+H]$^+$. Anal. Calcd. for C$_{22}$H$_{19}$N$_3$O$_5$; C, 65.18; H, 4.72; N, 10.37. Found: C, 64.47; H, 5.04; H, 10.24.

PREPARATION OF EXAMPLE 2

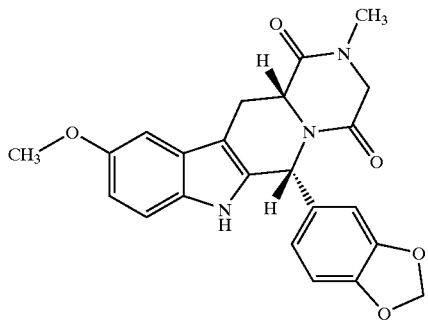

Example 2 was prepared from 5-methoxy-DL-tryptophan as depicted in the following synthetic scheme. 5-Methoxy-DL-tryptophan is a commercially available compound from Aldrich Chemical Co., Milwaukee, Wis.

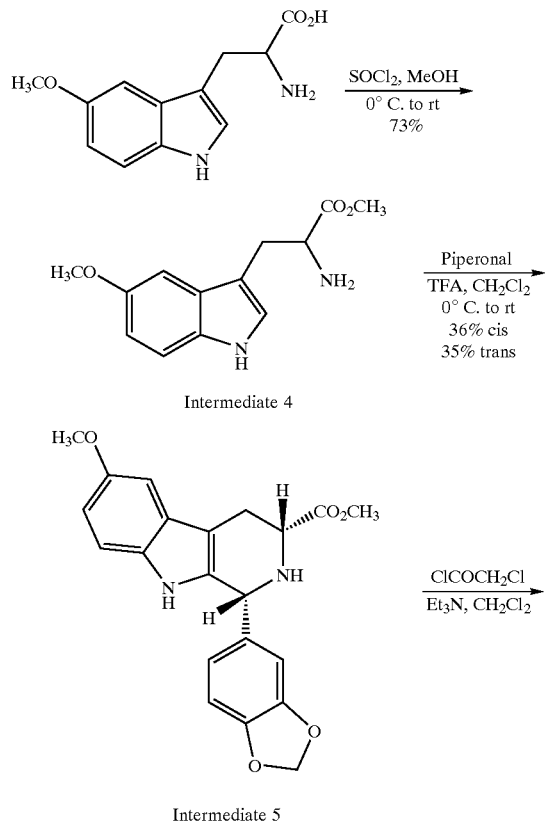

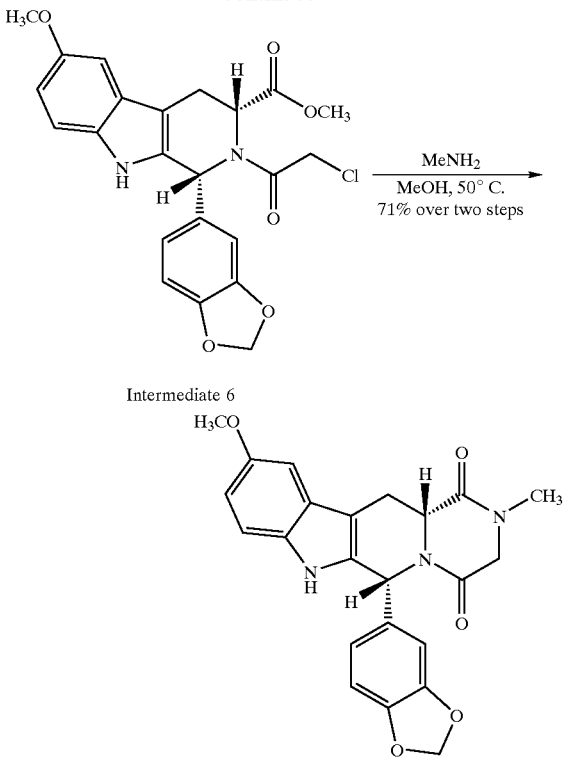

Intermediate 4

Preparation of 5-Methoxy-DL-tryptophan methyl ester

Thionyl chloride (1.0 mL, 13.7 mmol) was added dropwise to a slurry of 5-methoxy-DL-tryptophan (2.0 g, 8.54 mmol) in anhydrous methanol (22 mL) at 0° C. under a nitrogen blanket. The resulting solution was warmed slowly to room temperature, stirred for 17 hours, then the solvent was removed under reduced pressure. The resulting residue was dissolved in water (20 mL), neutralized with saturated NaHCO$_3$ (10 mL), and extracted twice with methylene chloride. The combined organic layers were dried over Na$_2$SO$_4$, filtered, and the solvent was removed under reduced pressure to provide 5-methoxy-DL-tryptophan methyl ester (Intermediate 4) as a light brown solid (1.55 g, 73%): $^1$H NMR (300 MHz, CDCl$_3$): δ 7.93 (bs, 1H), 7.30–7.25 (m, 1H), 7.09–7.03 (m, 1H), 6.90–6.83 (m, 1H), 3.90–3.78 (m, 4H), 3.72 (s, 3H), 3.30–3.20 (m, 1H), 3.10–2.98 (m, 1H).

Intermediate 5

Preparation of the (+/−)-cis-β-Carboline

Trifluoroacetic acid (0.65 mL, 8.48 mmol) was added to a mixture of Intermediate 4 (1.6 g, 6.45 mmol) and piperonal (1.17 g, 7.74 mmol) in methylene chloride (30 mL) at 0° C. under a nitrogen blanket. The resulting mixture was warmed to room temperature then stirred for 48 hours. The reaction mixture was diluted with methylene chloride (70 mL), then neutralized with saturated NaHCO$_3$ (15 mL). The organic layer was concentrated under reduced pressure, and the residue was purified by flash column chromatography, eluting with methylene chloride/ethyl acetate (8:1), to provide Intermediate 5 as a yellow solid (882 mg. 36%): TLC R$_f$(4:1 methylene chloride/ethyl acetate)=0.69; $^1$H NMR (300 MHz, CDCl$_3$): δ 7.32 (bs, 1H), 7.14 (d, J=8.7 Hz, 1H), 7.00 (S, 1H), 6.93–6.80 (m, 4H), 5.97 (S, 2H), 5.18 (s, 1H), 4.02–3.94 (m, 1H), 3.88 (s, 3H), 3.84 (s, 3H), 3.27–3.16 (m, 1H), 3.07–2.96 (m, 1H). The trans carboline also was obtained as a yellow solid, but was not characterized (850 mg, 35%): TLC $R_f$ (4:1: methylene chloride/ethyl acetate)=0.40.

Intermediate 6

Preparation of the (+/−)-cis-2-Chloroacetyl-β-carboline

Chloroacetyl chloride (0.21 mL, 2.60 mmol) was added dropwise to a mixture of Intermediate 5 (880 mg, 2.17 mmol) and triethylamine (0.36 mL, 2.60 mmol) in methylene chloride (18 mL) at 0° C. under a nitrogen blanket, and the resulting mixture was stirred at 0° C. for 2 hours. The resulting solution then was diluted with methylene chloride (60 mL), washed with saturated NaHCO$_3$ (10 mL), dried over sodium sulfate, filtered, and the solvent was removed under reduced pressure to provide Intermediate 6 as a yellow foam which was used without purification (1.14 g): TLC $R_f$ (4:1 methylene chloride/ethyl acetate)=0.92.

EXAMPLE 2

Preparation of (trans)-6-(1,3-Benzodioxol-5-yl)-10-methoxy-2-methyl-2,3,6,7,12,12a-hexahydropyrazino[1',2':1,6]pyrido[3,4-b]indole-1,4-dione A mixture of crude Intermediate 6 (1.14 g, 2.17 mmol) and methylamine (5 mL, 2.0 M in THF, 10 mmol) in methanol (12 mL) was heated at 50° C. under a nitrogen blanket for 6 hours, after which the mixture was stirred at room temperature for 17 hours. The resulting precipitate was isolated by vacuum filtration, then the solid was washed with methanol (2×5 mL) and dried in a vacuum oven at 60° C. for 24 hours to provide Example 2 as a white powder (0.65 g, 71% over two steps): mp 259–261° C.; TLC $R_f$ (4:1 methylene chloride/ethyl acetate)=0.35; $^1$H NMR (300 MHz, DMSO-d$_6$): δ 10.81 (s, 1H), 7.18 (d, J=8.8 Hz, 1H), 7.09 (d, J=1.5 Hz, 1H), 6.85 (s, 1H), 6.78 (s, 2H), 6.72–6.62 (m, 1H), 6.10 (s, 1H), 5.93 (s, 2H), 4.43–4.32 (m, 1H), 4.18 (d, J=17.2 Hz, 1H), 3.94 (d, J=17.2 Hz, 1H), 3.57–3.45 (m 1H), 3.01–2.82 (m, 4H): $^{13}$C NMR (75 MHz, DMSO-d$_6$) δ: 166.8, 166.6, 153.4, 147.0, 146.0, 137.0, 134.5, 131.1, 126.1, 119.2, 111.9, 111.2, 107.9, 106.9, 104.6, 100.8, 100.2, 55.5, 55.3, 55.2, 51.4, 32.8, 23.2 ppm; CI MS (methane) m/z 420 [C$_{23}$H$_{21}$N$_3$O$_5$+H]$^+$. Anal. Calcd. for C$_{23}$H$_{21}$N$_3$O$_5$: C, 65.86; H, 5.05; N, 10.02. Found: C, 65.75; H, 4.95; N, 9.91. The relative stereochemistry of Example 2 was confirmed to be cis isomer by an NOE difference experiment (DMSO-d$_6$): a positive NOE enhancement (2.3%) from the C12a proton at 4.37 ppm to the C6 proton at 6.12 ppm.

PREPARATION OF EXAMPLE 3

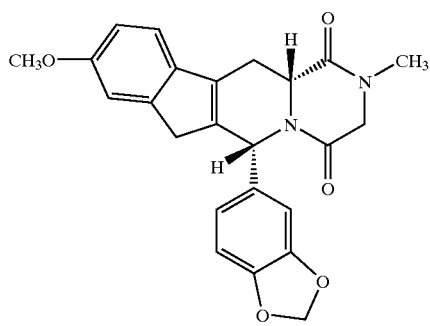

Example 3 was prepared from 6-methoxy-D-tryptophan ethyl ester as depicted in the following synthetic scheme. 6-Methoxy-D-tryptophan ethyl ester is a commercially available compound from Aldrich Chemical Col, Milwaukee, Wis.

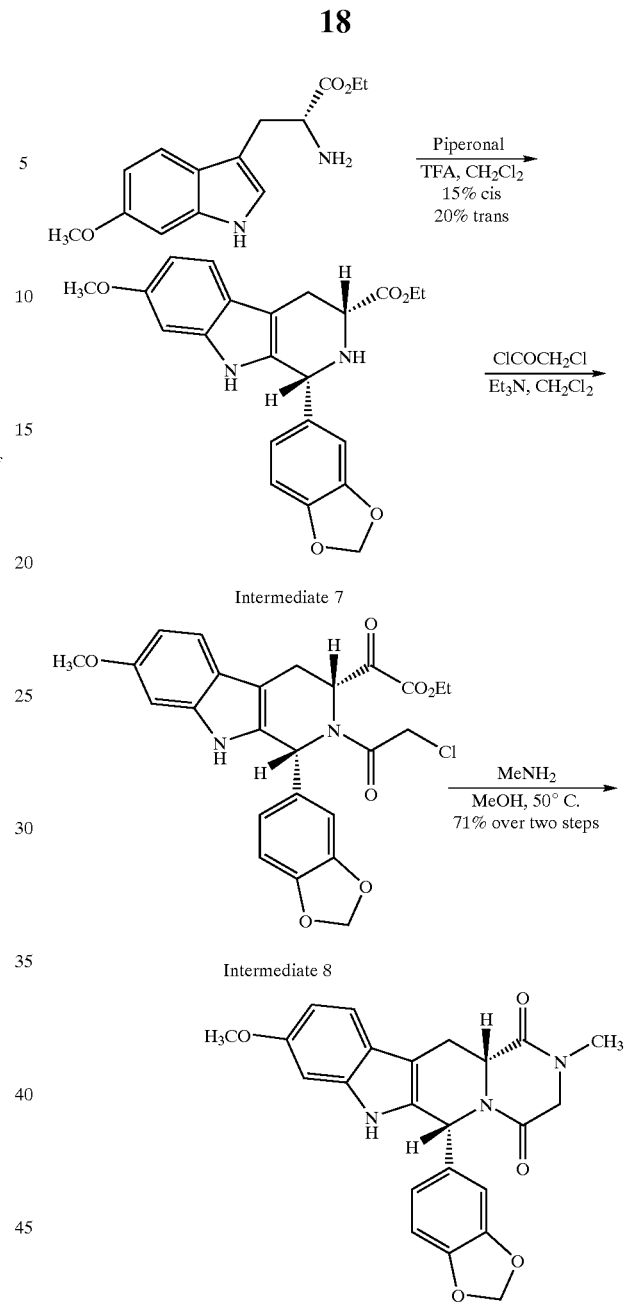

Intermediate 7

Preparation of a cis-β-Carboline

Trifluoroacetic acid (0.295 mL, 3.82 mmol) was added to a mixture of 6-methoxy-D-tryptophan ethyl ester (500 mg, 1.91 mmol) and piperonal (573 mg, 3.82 mmol) in methylene chloride (15 mL) at 0° C. under a nitrogen blanket, after which the mixture was warmed to room temperature overnight, then stirred for 3 days. The reaction mixture then was diluted with methylene chloride (30 mL) and neutralized with saturated NaHCO$_3$ (5 mL). The organic layer then was washed with brine (5 mL), dried over Na$_2$SO$_4$, filtered, and the solvent was removed under reduced pressure to provide a brown solid residue. The residue was purified by flash column chromatography, eluting with methylene chloride/ethyl acetate (10:1), to provide Intermediate 7 as a yellow solid (120 mg, 15%): TLC $R_f$ (10:1 methylene chloride/ethyl acetate)=0.57; $^1$H NMR (300 MHz, CDCl$_3$):

δ 7.42–7.30 (m, 2H), 6.90–6.70 (m, 6H), 5.94 (s, 2H), 5.13 (s, 1H), 4.31–4.19 (m, 2H), 3.93–3.86 (m, 1H), 3.79 (s, 3H), 3.20–3.10 (m, 1H), 3.00–2.89 (m, 1H), 1.35 (t, J=8.5 Hz, 3H). The trans-β-carboline also was obtained as a yellow solid, but was not characterized (160 mg, 20%): TLC R$_f$ (10:1 methylene chloride/ethyl acetate)=0.29.

Intermediate 8

Preparation of a cis-2-Chloroacetyl-β-carboline

Chloroacetyl chloride (0.030 mL, 0.373 mmol) was added dropwise to a mixture of Intermediate 7 (120 mg, 0.28.7 mmol) and triethylamine (0.052 mL, 0.373 mmol) in methylene chloride (5 mL) at 0° C. under a nitrogen blanket, and the resulting mixture was stirred at 0° C. for 1.5 hours. The brown solution then was diluted with methylene chloride (30 mL), washed with saturated NaHCO$_3$ (5 mL) and brine (5 mL), and the solvent was removed under reduced pressure to provide Intermediate 8 as a yellow solid which was used without further purification (179 mg): TLC R$_f$ (4:1 methylene chloride/ethyl acetate)=0.92.

EXAMPLE 3

Preparation of (6R,12aR)-6-Benzo[1,3]dioxol-5-yl-9-methoxy-2-methyl-2,3,6,7,12,12a-hexahydropyrazino-[1',2':1,6]pyrido[3,4-b]indole-1,4-dione A mixture of crude Intermediate 8 (179 mg) and methylamine (0.5 mL, 2.0M in THF, 1.0 mmol) in THF (3 mL) and methanol (5 mL) was heated at 50° C. under a nitrogen blanket for 6 hours. A second portion of methylamine (0.25 mL, 0.5 mmol) was added, and the resulting mixture was stirred at 40° C. for an additional 16 hours. The resulting orange slurry was cooled to room temperature, then the mixture was concentrated to about 5 mL. The resulting precipitate was isolated by vacuum filtration. The solid then was washed with methanol (3×2 mL) and dried in a vacuum oven at 70° C. to provide Example 3 as an off-white powder (0.085 g, 71% over two steps): mp 288–293° C.; TLC R$_f$(4:1 methylene chloride/ethyl acetate)=0.38; $^1$H NMR (300 MHz, DMSO-d$_6$): δ 10.81 (s, 1H), 7.42 (d, J=8.6 Hz, 1H), 6.84 (s, 1H), 6.80 (s, 1H), 6.77 (s, 2H), 6.65 (dd, J=8.6, 2.1 Hz, 1H), 6.09 (s, 1H), 5.92 (s, 2H), 4.38 (dd, J=11.6, 4.3 Hz, 1H), 4.17 (d, J=19.4 Hz, 1H), 3.93 (d, J=19.4 Hz, 1H), 3.73 (s, 3H), 3.46 (dd, J=15.9, 4.5 Hz, 1H), 3.00–2.87 (m, 4H); API m/z 420 [C$_{23}$H$_{21}$N$_3$O$_5$+H]$^+$; [α]$_D^{25°\ C.}$=+136.7° (c=0.25, DMSO). Anal. Calcd. for C$_{23}$H$_{21}$N$_3$O$_5$: C, 65.86; H, 5.05; N, 10.02. Found: C, 65.96; H, 4.97; N, 9.91. The stereochemistry of Example 3 was confirmed to be the desired cis isomer by a series of NOE difference experiments: a positive NOE enhancement from the C12a proton at 4.38 ppm to the C6 proton at 6.09 ppm; a positive NOE enhancement from the C6 proton at 6.09 ppm to the C12a proton at 4.38 ppm. Chiral HPLC analysis (Chiralcel OD Column, 250×4.6 mm, Retention Time=20.9 minutes; 1:1 isopropanol/hexanes; flow=1.0 mL/minute; detector@220 nm; 25° C.) showed one major peak, with a purity of 99.8%.

PREPARATION OF EXAMPLE 4

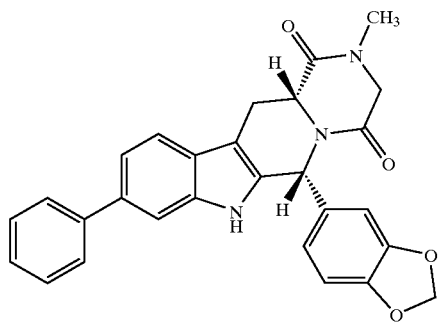

Example 4 was prepared from 6-bromo-DL-tryptophan ethyl ester hydrochloride, i.e., Intermediate 9, as depicted in the following synthetic scheme. Intermediate 9 was prepared from 4-bromo-2-nitrotoluene in four well-known synthetic steps. 4-Bromo-2-nitrotoluene is a commercially available compound from Aldrich Chemical Co., Milwaukee, Wis.

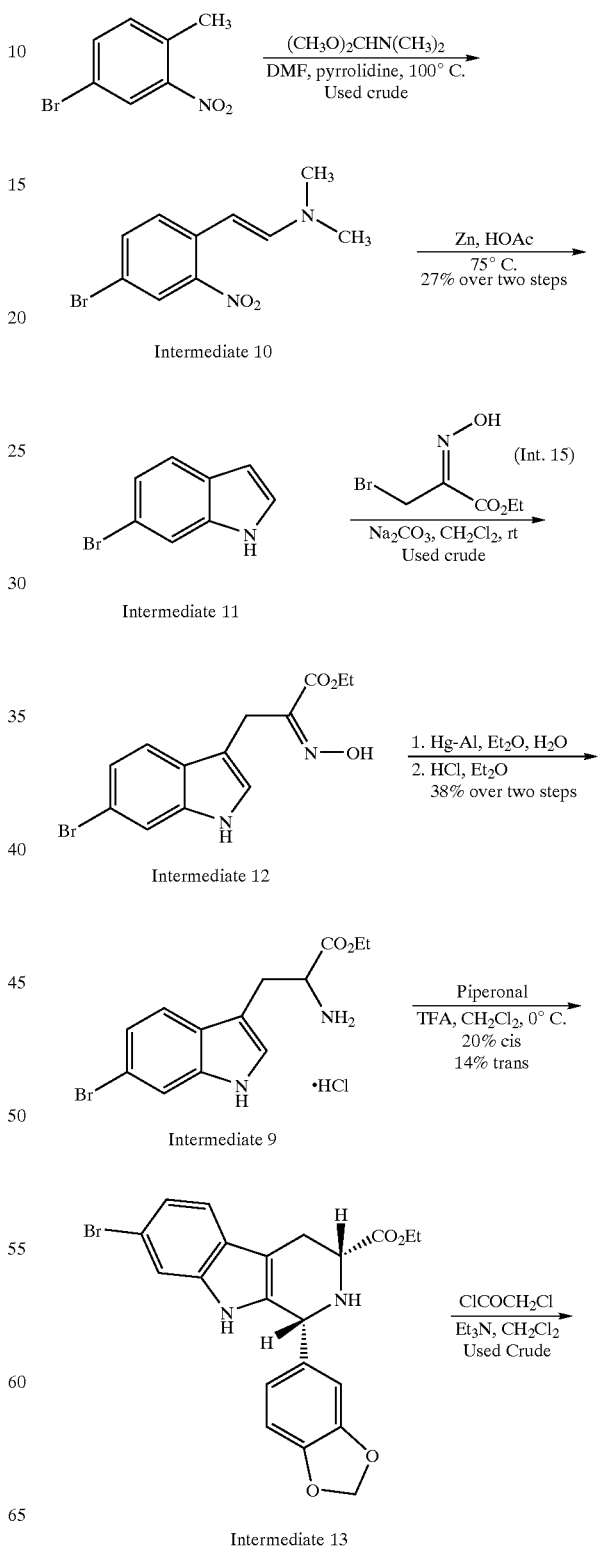

-continued

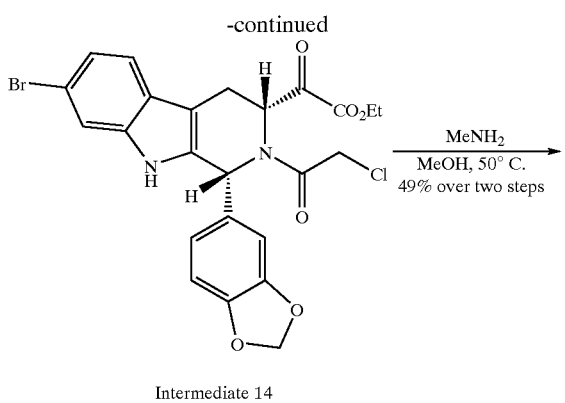

Intermediate 14

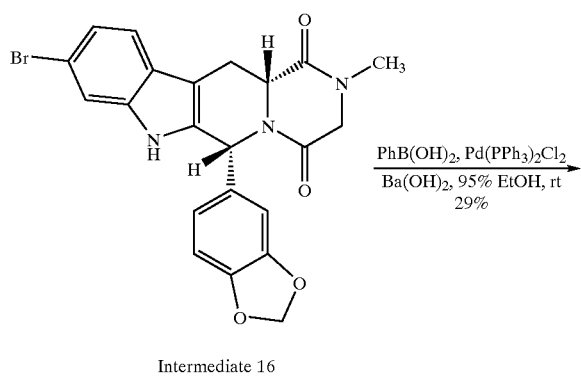

Intermediate 16

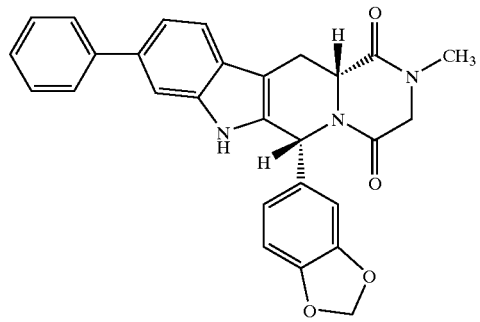

Example 4

Intermediate 11
Preparation of 6-Bromoindole

The synthesis of Intermediate 11 is disclosed in M. P. Moyer et al., *J. Org. Chem.*, 51, page 5106 (1986); and K. L. Rinehart et al., *J. Am. Chem. Soc.*, 109, page 3378 (1987).

A mixture of 4-bromo-2-nitrotoluene (20 g, 93 mmol), pyrrolidine (8 mL, 93 mmol), and N,N-dimethylformamide dimethyl acetal (37 mL, 278 mmol) in anhydrous N,N-dimethylformamide (200 mL) was heated at 110° C. under a nitrogen blanket for 2 hours. The mixture was cooled, then diluted with water (1.5 L) and extracted with ether (3×500 mL). The combined organic extracts were washed with brine (500 mL), dried over $Na_2SO_4$, and filtered. The solvent was removed under reduced pressure to provide Intermediate 10 as dark purple crystals which were suitable for use without further purification (27.9 g): TLC $R_f$ (1:4 ethyl acetate/chloroform)=0.77.

Zinc granules (30 g, 459 mmol) were added over 30 minutes to a solution of crude Intermediate 10 (25 g, 93 mmol) in acetic acid (400 mL) and water (100 mL) at 75° C., after which the mixture was stirred for an additional 1 hour. The suspension was cooled, filtered, and extracted with ethyl acetate (2×2 L). The combined organic extracts were washed with water (2×2 L), saturated $NaHCO_3$ solution (2×500 mL), and brine (2×500 mL), dried over magnesium sulfate ($MgSO_4$), and filtered. The solvent was removed under reduced pressure to yield a purple residue which was purified by flash column chromatography, eluting with hexanes/methylene chloride (1:1), to provide 6-bromoindole (Intermediate 11) as a blue-white powder (4.9 g, 27% over two steps): TLC $R_f$ (1:9 ethyl acetate/chloroform)=0.81. The proton NMR spectrum (300 MHz, $CDCl_3$) was identical to the known compound.

Intermediate 9
Preparation of 6-Bromo-DL-tryptophan ethyl ester hydrochloride

The synthesis of Intermediate 12 is disclosed in T. L. Gilchrist et al., *J. Chem. Soc., Chem. Commun.*, page 1089 (1979); U. Schmidt et al., *Liebigs Ann. Chem.*, page 785 (1985); and U. Schmidt et al., *Tetrahedron Lett.*, 23, page 4911 (1982).

Ethyl bromopyruvate (10 mL, 80 mmol) was added dropwise to a biphasic mixture of hydroxyl-amine sulfate (6.6 g, 40 mmol) in water (50 mL) and chloroform (50 mL), and the mixture was stirred at room temperature for 3 hours. The mixture was filtered, and the organic phase was concentrated under reduced pressure to yield the oxime Intermediate 15 as a white solid, which was used without further purification (15.9 g, 95%): TLC $R_f$ (1:4 ethyl acetate/chloroform)=0.12.

Powdered sodium carbonate (4.0 g, 37 mmol) was added to a dark green solution of Intermediate 11 (4.9 g, 25 mmol) and Intermediate 15 (7.9 g, 37 mmol) in methylene chloride (50 mL) at room temperature under a nitrogen blanket. The mixture was stirred for 7 hours, after which the mixture was diluted with ethyl acetate (150 mL), washed with brine (100 mL), dried over $MgSO_4$, and filtered. The solvents were removed under reduced pressure to provide Intermediate 12 as a dark green oil which was suitable for use without further purification (9.6 g): TLC $R_f$ (1:9 ethyl acetate/chloroform)=0.18.

Aluminum amalgam was prepared by sequentially dipping several pieces of aluminum foil (5 g total) in 1 N sodium hydroxide, saturated mercury (II) chloride solution, water, and ethanol. The aluminum pieces then were added to a solution of crude Intermediate 12 in ether (100 mL) and water (5 mL) at room temperature. The gray suspension was stirred for 24 hours, then filtered. The organic layer was washed with brine (100 mL), dried over $Na_2SO_4$, and filtered. The solvents were removed under pressure to provide a dark green residue, which was treated with a ethereal HCl (1 M in ether). The solid was collected by vacuum filtration, and dried in a vacuum oven at 60° C. overnight to provide Intermediate 9 as a darkred powder (3.3 g, 38% over two steps): $^1H$ NMR (300 MHz, DMSO-$d_6$): δ 11.21 (s, 1H), 8.40 (s, 2H), 7.57 (s, 1H), 7.48 (d, J=8.4 Hz, 1H), 7.27 (s, 1H), 7.16 (d, J=7.0 Hz, 1H), 4.24–4.18 (m, 3H), 4.09 (q, J=6.8 Hz, 2H), 1.10 (t, J=7.3 Hz, 3H).

Intermediate 13
Preparation of a cis-β-carboline

A solution of saturated aqueous sodium carbonate (50 mL) was added to a dark green solution of Intermediate 9 (3.4 g, 10 mmol) in methylene chloride (100 mL), and the resulting mixture was shaken for 10 minutes. The organic layer then was dried over $Na_2SO_4$ and filtered. The solution was concentrated under reduced pressure to a volume of 20 mL and cooled to 0° C. under a nitrogen blanket. Piperonal (1.7 g, 12 mmol) was added to the solution, followed by the addition of trifluoroacetic acid (1.5 mL, 20 mmol), after which the solution was warmed to room temperature overnight. The reaction mixture then was diluted with ethyl acetate, and neutralized with aqueous NaHCO$_3$ (100 mL). The organic layer was washed with brine (50 mL), dried over Na$_2$SO$_4$, filtered, and the solvent was removed under reduced pressure to provide a brown oil. This residue was purified by flash column chromatography, eluting with ethyl acetate/chloroform (1:19), to provide Intermediate 13 as a light yellow solid (0.88 g, 20%): TLC R$_f$ (1:9 ethyl acetate/chloroform)=0.60; $^1$H NMR (300 MHz, DMSO-d$_6$): δ 10.48 (s, 1H), 7.42 (s, 1H), 7.37 (d, J=10.0 Hz, 1H), 7.09 (d, J=9.9 Hz, 1H), 6.90 (d, J=6.2 Hz, 2H), 6.83 (s, 1H), 6.00 (s, 2H), 5.15 (s, 1H), 4.16 (q, J=6.3 Hz, 2H), 3.85–3.80 (m, 1H), 2.90–2.80 (m, 1H), 1.24 (t, J=6.9 Hz, 3H). The trans-β-carboline also was obtained as a light yellow solid, but was not characterized (0.60 g, 14%): TLC R$_f$ (1:9 ethyl acetate/chloroform)=0.33.

Intermediate 14

Preparation of a cis-2-chloroacetyl-β-carboline

Chloroacetyl chloride (0.2 mL, 2.6 mmol) was added dropwise to a solution of Intermediate 13 (0.88 g, 2.0 mmol) and triethylamine (0.4 mL, 2.6 mmol) in methylene chloride (10 mL) at 0° C. under a nitrogen blanket. The mixture was slowly warmed to room temperature and stirred for 5 hours. The resulting white suspension was diluted with methylene chloride (100 mL), washed with brine (100 mL), dried over Na$_2$SO$_4$, and filtered. The solvent was removed under reduced pressure to provide Intermediate 14 as an amber foam, which was used without further purification (1.03 g): TLC R$_f$ (1:9 ethyl acetate/chloroform)=0.76.

Intermediate 16

A mixture of crude Intermediate 14 (1.0 g, 1.9 mmol) and methylamine (4 mL, 7.7 mmol, 2.0 M in THF) in methanol (10 mL) was heated at reflux under a nitrogen blanket for 2 hours, after which the resulting orange suspension was cooled to room temperature. The solids were collected by vacuum filtration and dried in a vacuum oven at 60° C. overnight to provide Intermediate 15 as a white powder (0.45 g, 49% over two steps): mp 324–330° C.; TLC R$_f$ (1:9 methanol/chloroform)=0.78; $^1$H NMR (300 MHz, DMSO-d$_6$): δ 11.18 (s, 1H), 7.53 (d, J=8.4 Hz, 1H), 7.49 (s, 1H), 7.14 (d, J=8.3 Hz, 1H), 6.86 (s, 1H), 6.78 (s, 2H), 6.11 (s, 1H), 5.93 (s, 2H), 4.39 (dd, J=4.4, 11.5 Hz, 1H), 4.17 (d, J=17.1 Hz, 1H), 3.95 (d, J=17.2 Hz, 1H), 3.52 (dd, J=4.5, 15.9 Hz, 1H), 3.01 (d, J=11.7 Hz, 1H), 2.93 (s, 3H); API MS m/z 470 [C$_{22}$H$_{18}$BrN$_3$O$_4$+H]$^+$. Anal. Calcd. for C$_{22}$H$_{18}$BrN$_3$O$_4$: C, 56.42; H, 3.87; N, 8.97. Found: C, 56.34; H, 3.92; N, 8.82. The sterochemistry of Intermediate 15 was confirmed to be the desired cis isomer by a series of NOE difference experiments: positive NOE enhancements from the C12a proton at 4.39 ppm to the C6 proton at 6.11 ppm and a C12 proton at 3.52 ppm; a positive NOE enhancement from the C6 proton at 6.11 ppm to the C12a proton at 4.39 ppm.

EXAMPLE 4

Preparation of (+–, cis)-6-Benzo[1,3]dioxol-5-yl-2-methyl-9-phenyl-2,3,6,7,12,12a-hexahydropyrazino[1',2':1,6]pyrido[3,4-b]indole-1,4-dione Phenyl boronic acid (0.09 g, 0.74 mmol) was added to a degassed mixture of Intermediate 16 (0.172 g, 0.37 mmol), barium hydroxide octahydrate (0.58 g, 1.85 mmol), and bis(triphenylphosphine)palladium (II) chloride (0.05 g, 0.07 mmol) in ethanol (10 mL), and the resulting mixture was stirred at room temperature for 48 hours. An additional portion of phenyl boronic acid (0.09 g, 0.74 mmol) then was added, after which the mixture was stirred at room temperature for an additional 12 hours. The palladium catalyst was removed by vacuum filtration through a plug of Celite, and the resulting filtrate was concentrated under reduced pressure and purified by flash column chromatography, eluting with methylene chloride/ethyl acetate (4:1), to provide a white solid. This solid was further purified by recrystallization from methylene chloride followed by vacuum filtration to yield a solid, which was dried overnight under vacuum at 60° C. to provide Example 4 as a white solid (0.049 g, 29%): mp 198–208° C.; TLC R$_f$ (1:4 ethyl acetate/chloroform)= 0.37; $^1$H NMR (500 MHz, CDCl$_3$): δ 7.91 (s, 1H), 7.46 (s, 1H), 7.37 (d, J=8.4 Hz, 2H), 7.27–7.25 (m, 4H), 6.95 (s, 1H), 6.79 (s, 1H), 6.72–6.67 (m, 2H), 5.93 (s, 2H), 5.29 (s, 1H), 4.34 (dd, J=4.0, 4.11 Hz, 1H), 4.12 (dd, J=1.2, 1.1 Hz, 1H), 3.51 (dd, J=4.2, 4.2 Hz, 1H), 3.00 (s, 3H), 2.93–2.88 (m, 2H) ppm; API MS m/z 467 [C$_{28}$H$_{23}$N$_3$O$_4$+H]$^+$. HPLC analysis (Symmetry C18 Column, 150×3.5 mm. Retention Time= 10.9 minutes; 30/0.85:70/0.1 acetonitrile/TFA:water/TFA to 100/0.85 acetonitrile/TFA over 20 minutes; flow=1.0 mL/min; detector at 220 nm; 25° C.) showed one peak, with a purity of 91.5%. Chiral HPLC analysis (Chiralcel OD Column, 250×4.6 mm, Retention Times=12.9 and 17.4 min; 1:1 isopropanol/hexanes; flow=0.5 mL/min; detector at 222 nm; 25° C.) showed two major peaks, with a ratio of 54:42 and with a total purity of 96.6%. The relative stereochemistry of Intermediate 4 was confirmed to be the desired cis isomer by a series of NOE difference experiments: a positive NOE enhancement from the C12a proton at 4.34 ppm to the C6 proton at 6.79 ppm; a positive NOE enhancement from the C6 proton at 6.79 ppm to the C12a proton at 4.34 ppm.

PREPARATION OF EXAMPLE 5

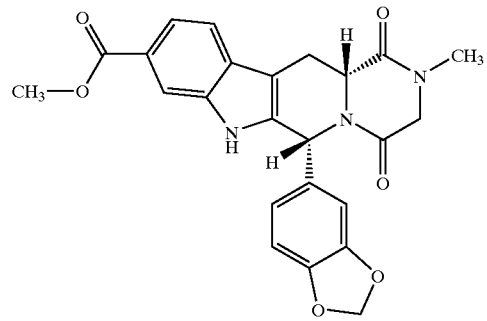

Example 5 was prepared from indole-6-carboxylic acid as depicted in the following synthetic scheme. Indole-6-carboxylic acid is a commercially available compound. Aspects of the following synthetic scheme are disclosed in Y. Yokoyama et al., *Tetrahydron Lett,* 40, p. 7803 (1990); and H.R. Snyder et al., *J. Am Chem. Soc.,* 77, p. 1257 (1955).

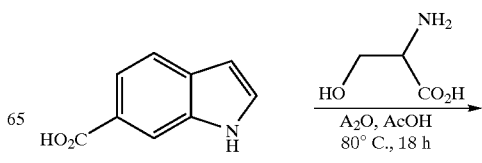

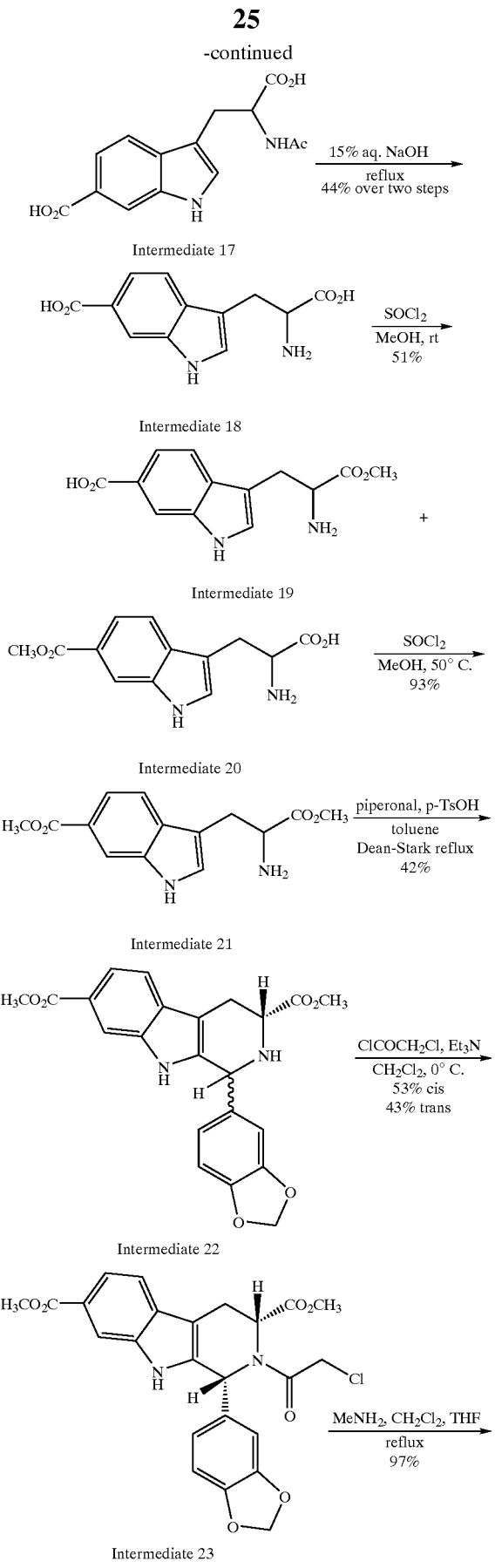

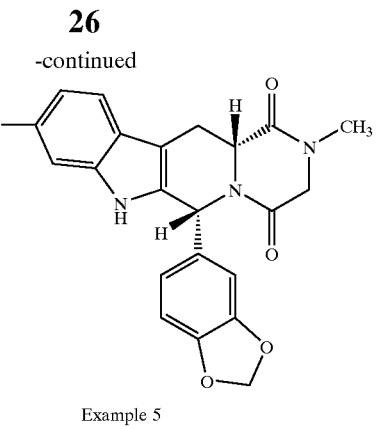

Example 5

Intermediate 17
Preparation of N-Acetyl-6-carboxytryptophan

A mixture of indole-6-carboxylic acid (5.0 g, 31 mmol), DL-serine (3.25 g, 31 mmol), and acetic anhydride (8.8 mL, 93 mmol) in glacial acetic acid (50 mL) was heated under a nitrogen blanket at 80° C. for 24 hours. The resulting brown solution was cooled to room temperature, then the solvent was removed under reduced pressure to provide Intermediate 17 as a brown foam, which was used without further purification (11.0 g): $^1$H NMR (300 MHz, $D_2O$): δ 8.08 (s, 1H), 7.72 (s, 2H), 7.40 (s, 1H), 4.61–4.53 (m, 1H), 3.45–3.35 (m, 1H), 3.23–3.13 (m, 1H), 1.92 (s, 3H) ppm.

Intermediate 18
Preparation of 6-Carboxytryptophan

A solution of crude Intermediate 17 (11.0 g) was heated in 15% aqueous sodium hydroxide for 18 hours. The reaction mixture was cooled to 0° C., then acidified to pH 5 with acetic acid, after which the solution was concentrated under reduced pressure. The residue was slurried in water (500 mL) then the solids were collected by filtration under reduced pressure and dried in a vacuum oven at 100° C. for 18 hours to yield Intermediate 18 as a gray solid (2.6 g, 34% over two steps). A second portion of Intermediate 18 was recovered from the filtrate (0.75 g, 10% over two steps): $^1$H NMR (300 MHz, DMSO-$d_6$): δ 11.30 (s, 1H), 8.00 (s, 1H), 7.68–7.52 (m, 2H), 7.40 (s, 1H), 3.50–3.40 (m, 1H), 3.39–3.25 (m, 1H), 3.10–2.92 (m, 1H) ppm.

Intermediates 19–21
Preparation of 6-Methylcarboxytryptophan

Thionyl chloride (0.84 mL, 11 mmol) was added dropwise to a suspension of Intermediate 18 (0.75 g, 302 mmol) in methanol (15 mL) at 0° C. under a nitrogen blanket, then the mixture was warmed to room temperature and stirred for 20 hours. The resulting solution was diluted with ethyl acetate (200 mL), extracted with saturated sodium bicarbonate ($NaHCO_3$) solution (2×50 mL) and acidified to pH 6 with acetic acid. The resulting slurry was filtered, then the solid was washed with several small portions of water, and dried in a vacuum oven at room temperature to yield a mixture of Intermediates 19 and 20 as a brown solid (400 mg, 51%).

Thionyl chloride (0.45 mL, 6.0 mmol) was added dropwise to a slurry of Intermediates 19 and 20 (316 mg, 1.21 mmol) in methanol (15 mL) at 0° C. under a nitrogen blanket. This mixture was warmed to room temperature and stirred for 3 hours, then the mixture was heated to 50° C. to stir for an additional 2 hours. The solvent was removed under reduced pressure, and the residue was diluted with ethyl acetate (200 mL). The solution was washed with saturated $NaHCO_3$ (20 mL), water (20 mL), and brine (20 mL), dried over $Na_2SO_4$, filtered, and the solvent was removed under reduced pressure to yield Intermediate 21 as a brown oil (310 mg, 93%): TLC $R_f$ (5:1 methylene chloride/ ethyl acetate)=0.1: $^1$H NMR (300 MHz, CDCl$_3$): δ 9.11 (bs, 1H), 8.07 (s, 1H), 7.80 (d, J=8.0 Hz, 1H), 7.61 (d, J=8.0 Hz, 1H), 7.19 (s, 1H), 3.93 (s, 3H), 3.90–3.82 (m, 1H), 3.71 (s, 1H), 3.31–3.22 (m, 1H), 3.13–3.05 (m, 1H) ppm.

Intermediate 22

Preparation of 5-Carboline

A mixture of Intermediate 21 (495 mg, 1.79 mmol), piperonal (479 mg, 3.2 mmol), and p-toluene sulfonic acid monohydrate (80 mg) was refluxed in toluene with water removal via Dean-Stark trap for 5 hours under a nitrogen blanket. The dark brown mixture was cooled to room temperature and diluted with ethyl acetate (250 mL). The mixture then was washed successively with saturated NaHCO$_3$ (30 mL), water (20 mL), and brine (20 mL), dried over Na$_2$SO$_4$, filtered, and the solvent was removed under reduced pressure. The residue was slurried in a mixture of methylene chloride/ethyl acetate (5:1, 10 mL) and the slurry was filtered under pressure to yield a mixture of the cis- and trans- Intermediate 22, which were used without characterization (311 mg, 42%).

Intermediate 23

Preparation of cis-2-Chloroacetyl-β-carboline

Chloroacetyl chloride (0.076 mL, 0.99 mmol) was added dropwise to a mixture of Intermediate 22 (311 mg, 0.76 mmol, mixture of cis and trans isomers) and triethylamine (0.138 mL, 0.99 mmol) in chloroform (10 mL) at 0° C. under a nitrogen blanket. The resulting mixture was stirred at 0° C. for 1 hour, then warmed to room temperature and stirred for an additional 2 hours. The solution was diluted with ethyl acetate (100 mL), washed with saturated NaHCO$_3$ solution (10 mL), water (10 mL), and brine (10 mL), dried over sodium sulfate (Na$_2$SO$_4$), and the solvent was removed under reduced pressure to provide a yellow foam. The mixture was purified by flash column chromatography, eluting with hexanes/ethyl acetate (2:1), to yield Intermediate 23 as a white solid, which was not characterized (195 mg, 53%): TLC R$_f$ (2:1 hexanes/ethyl acetate)=0.62. The latter eluting trans-2-chloroacetyl-β-carboline was obtained as a white solid which also was not characterized (160 mg, 43%): TLC R$_f$ (2:1 hexanes/ethyl acetate)=0.40.

EXAMPLE 5

Preparation of (+−, cis)-6-Benzo[1,3]dioxol-5-yl-2-methyl-1,4-dioxo-1,2,3,6,7,12,12a-octahydropyrazino[1',2':1,6]pyrido[3,4-b]indole-9-carboxylic acid methyl ester A mixture of Intermediate 23 (132 mg, 0.27 mmol) and methylamine (6.2 mL, 12.4 mmol, 2 M solution in THF) in methylene chloride (18 mL) was refluxed under a nitrogen blanket for 4 hours. The resulting solution was concentrated under reduced pressure to yield a yellow solid, which was stirred in methanol (4 mL) for 1 hour. The solid was isolated by filtration under reduced pressure, washed with methanol (5×1 mL), and dried in a vacuum oven at 70° C. for 17 hours to provide Example 5 as an off-white solid (117 mg, 96%): mp 294–295° C.; TLC R$_f$ (5:1:0.5 methylene chloride/ethyl acetate/methanol)=0.65; $^1$H NMR (300 MHz, CDCl$_3$): δ 8.25 (bs, 1H), 8.03 (s, 1H), 7.84 (d, J=8.7 Hz, 1H), 7.60 (d, J=8.7 Hz, 1H), 6.86 (dd, J=8.0, 1.7 Hz, 1H), 6.73 (d, J=1.7 Hz, 1H), 6.69 (d, J=8.0 Hz, 1H), 6.20 (s, 1H), 5.88 (s, 1H), 5.86 (s, 1H), 4.30 (dd, J=11.6, 4.5 Hz, 1H), 4.11 (dd, J=17.6, 1.3 Hz, 1H), 4.00–3.88 (m, 4H), 3.78 (dd, J=16.1, 4.5 Hz, 1H), 3.27–3.16 (m, 1H), 3.05 (s, 3H) ppm; CI MS m/z 448 [C$_{24}$H$_{21}$N$_3$O$_6$+H]$^+$, Anal. Calcd. for C$_{24}$H$_{21}$N$_3$O$_6$: C, 64.42; H, 4.73; N, 9.39. Found: C, 64.12; H, 4.61; N, 9.12. HPLC analysis (Aquasil C18 Column, 100×4.6 mm, Retention Time=10.3 minutes; 45:55/0.03 acetonitrile:water/TFA; flow=0.50 mL/min.; detector @ 254 nm; temperature ambient) showed one peak, with a purity of 99.7%. The stereochemistry of Example 5 was confirmed to be the cis isomer by a series of NOE difference experiments: a positive NOE enhancement from the C12a proton at 4.30 ppm to the C6 proton at 6.20 ppm; a positive NOE enhancement from the C6 proton at 6.20 ppm to the C12a proton at 4.30 ppm.

PREPARATION OF EXAMPLE 6

(+−,trans)-6-Benzo[1,3]dioxol-5-yl-2-methyl-1,4-dioxo-1,2,3,4,6,7,12,12a-octahydropyrazino[1',2':1,6]pyrido[3,4-b]indole-9-carobxylic acid

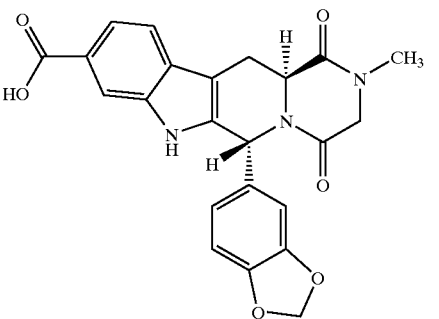

Example 6 was prepared from Example 5 by the following procedure.

A mixture of Example 5 (0.125 g, 0.28 mmol), 2 N sodium hydroxide solution (2 mL), THF (6 mL), and methanol (2 mL) was heated at 80° C. for 24 hours. The resulting yellow solution was cooled to room temperature and diluted with water, then the solution was acidified to pH 6 with acetic acid. The resulting solution was concentrated under reduced pressure to a volume of 20 mL, and was allowed to stand overnight at room temperature. The resulting solid precipitate was isolated by filtration under reduced pressure, then further purified by stirring in diethyl ether (4 mL) at 40° C. for 2 hours. The resulting solids were isolated by filtration under reduced pressure, washed with diethyl ether (5×1 mL), and dried in a vacuum oven at 90° C. for 4 hours to provide Example 6 as an off-white solid (0.093, 78%): mp 246–252° C.; $^1$H NMR (300 MHz, CD$_3$OD): δ 8.05 (s, 1H), 7.76 (d, J=8.6 Hz, 1H), 7.56 (d, J=8.14 Hz, 1H), 6.99 (s, 1H), 6.83–6.73 (m, 2H), 6.66 (dd, J=8.0 Hz, 1H), 5.93 (s, 2H), 4.34–4.23 (m, 2H), 4.08 (d, J=17.3 Hz, 1H), 3.44 (dd, J=15.4, 4.2 Hz, 1H), 3.08–2.95 (m, 4H) ppm; ESI MS m/z 432 [C$_{23}$H$_{19}$N$_3$O$_6$—H]$^+$. Anal. Calcd for C$_{23}$H$_{19}$N$_3$O$_6$: C, 63.74; H, 4.42; N, 9.70. Found: C, 62.77; H, 4.61; N, 9.19. HPLC analysis (Aquasil C18 Column, 100×4.6 mm, Retention Time=25.4 minutes; 30:70/0.03 acetonitrile:water/TFA; flow=0.50 mL/min; detector at 254 nm; temperature ambient) showed one peak, with a purity of 98.9%. The stereochemistry of Example 6 was confirmed to be the trans isomer by a series of NOE difference experiments: no NOE enhancement from the C12a proton at 4.30 ppm to the C6 proton at 6.99 ppm; no NOE enhancement from the C6 proton at 6.99 ppm to the C12a proton at 4.30 ppm.

PREPARATION OF EXAMPLE 7

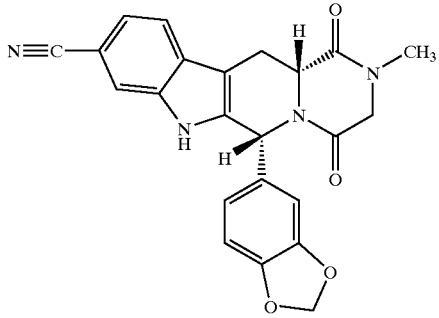

Example 7 was prepared from 6-cyanoindole as depicted in the following synthetic scheme. 6-Cyanoindole is a commercially available compound

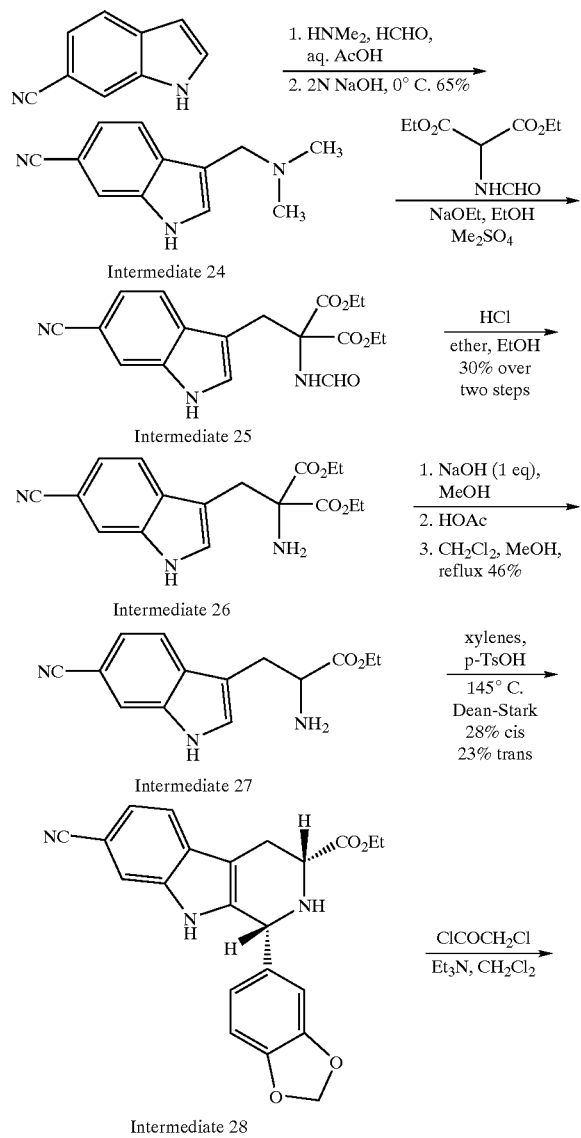

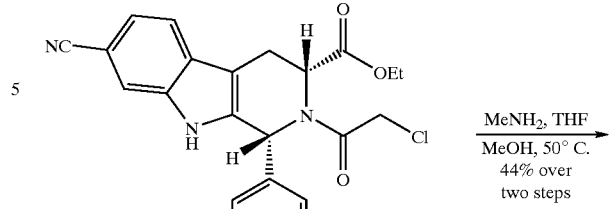

Intermediate 29

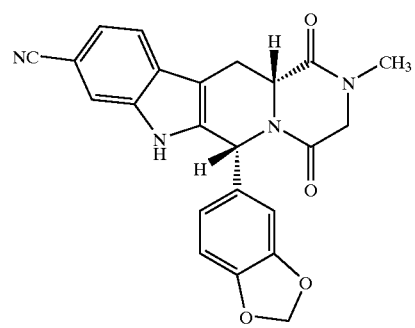

Example 7

Intermediate 24
Preparation of Gramine

Acetic acid (6 ml) was added dropwise to aqueous dimethylamine (7.0 ml, 55.7 mmol) at a rate that maintained the solution below 5° C. To this mixture was added aqueous formaldehyde (4.2 ml, 55.7 mmol) dropwise. The resulting mixture then was added to a solution of 6-cyanoindole (6.6 g, 46.4 mmol) in acetic acid (30 ml) over 15 minutes at room temperature under a nitrogen blanket. The resulting dark yellow solution was stirred at room temperature for 3 hours, followed by dilution with 2 N sodium hydroxide (30 ml), then stored at 0° C. for 12 hours. The solution was decanted, and the solvent was removed under reduced pressure to produce a white foam. The white foam was dissolved in water (200 mL), and adjusted to a basic pH with a saturated $NaHCO_3$ solution. The resulting mixture was extracted with ethyl acetate (3×200 mL), dried over $Na_2SO_4$, and the solvent was removed under reduced pressure to yield Intermediate 24 as an off-white solid (6.24 g, 65%): $^1$H NMR (300 MHz, DMSO-$d_6$): δ 11.52 (s, 1H), 7.85 (s, 1H), 7.77 (d, J=8.2 Hz, 1H), 7.54 (d, J=2.4 Hz, 1H), 7.31 (dd, J=1.5, 8.3 Hz, 1H), 3.56 (s, 2H), 2.13 (s, 6H) ppm.

Intermediate 25
Preparation of Diester

To a solution of diethyl formamidomalonate (6.61 g, 32.5 mmol) in ethanol (40 mL) under an argon blanket was added sodium ethoxide (12.0 mL, 32.5 mmol, 2.7 M solution in ethanol). The resulting mixture was stirred at room temperature for 30 minutes to yield a slurry. To the slurry was added Intermediate 24 (5.39 g, 27.1 mmol), followed by dimethyl sulfate (5.1 mL, 54.2 mmol). The resulting clear brown solution was stirred at room temperature, and after 15 minutes a precipitate formed. The resulting slurry was stirred at room temperature for 16 hours. Then the solids were removed by filtration under reduced pressure, and the filtrate concentrated to yield diethyl ester Intermediate 25 as an orange solid which was used without further purification (10.9 g): TLC $R_f$ (4:1 methylene chloride/ethyl acetate)= 0.50.

Intermediate 26

Preparation of Amino Diester

To a solution of Intermediate 25 (27.1 mmol) in methanol (120 mL) was added hydrochloric acid in diethyl ether (54 mL, 54.2 mmol, 1 M solution in diethyl ether). The resulting solution was allowed to sit overnight under an argon blanket. The mixture then was concentrated under reduced pressure, diluted with ethyl acetate (100 mL), and extracted with 2 N HCl (3×200 mL). The combined aqueous extracts were adjusted to pH 8 with $Na_2CO_3$, followed by extraction with methylene chloride (3×200 mL). The combined organic extracts were dried over $Na_2SO_4$, and the solvent was removed under reduced pressure to provide Intermediate 26 as an orange oil (2.57 g, 30%): $^1$H NMR (300 MHz, $CDCl_3$): δ 8.79 (bs, 1H), 7.69–7.64 (m, 2H), 7.34–7.30 (m, 2H), 4.27–4.15 (m, 4H), 3.48 (s, 2H), 1.99 (bs, 2H), 1.31–1.23 (m, 6H) ppm.

Intermediate 27

Preparation of (+/−)-6-Cyanotryptophan Ethyl Ester

To a mixture of Intermediate 26 (2.57 g, 7.80 mmol) in ethanol (80 mL) was added a solution of sodium hydroxide (0.37 g, 9.25 mmol) in water (5 mL). The resulting orange solution was stirred at room temperature for 16 hours, after which an additional 0.5 equivalents of sodium hydroxide in water was added. The mixture was stirred for 5 hours, then acidified to pH 6 with acetic acid. Concentration of the solution under reduced pressure provided an oil which was dissolved in 2:1 methylene chloride/methanol (60/20 mL), then heated at reflux for 5 hours. The resulting slurry was cooled, then the solids were removed by filtration under reduced pressure. The filtrate was concentrated, dissolved in water (100 mL), then extracted with methylene chloride (3×100 mL). The organic extracts were dried over $Na_2SO_4$, and the solvent was removed under reduced pressure to provide Intermediate 27 as an orange oil (0.91 g, 46%): $^1$H NMR (500 MHz, DMSO-$d_6$): δ 11.40 (s, 1H), 7.81 (s, 1H), 7.68 (d, J=10.0 Hz, 1H), 7.45 (s, 1H), 7.30 (d, J=10.0 Hz, 1H), 4.00–3.96 (m, 2H), 3.60–3.57 (m, 1H), 3.03–2.94 (m, 2H), 2.08 (bs, 2H), 1.10–1.07 (m, 3H) ppm.

Intermediate 28

Preparation of (+/−)-cis-β-Carboline

A solution of Intermediate 27 (0.49 g, 1.9 mmol), piperonal (0.37 g, 2.5 mmol) and p-toluene-sulfonic acid monohydrate (0.050 g, 0.26 mmol) in xylenes (30 mL) was heated at 145° C. under an argon blanket for 16 hours with water removal via Dean-Stark trap. The resulting orange solution was cooled, diluted with methylene chloride (10.0 mL), then washed with saturated $NaHCO_3$ (20 mL). The organic layer was dried over $Na_2SO_4$, then the solvent was removed under reduced pressure to provide an orange oil. The residue was purified by flash column chromatography, eluting with methylene chloride/ethyl acetate (6:1) to provide Intermediate 28 as orange solid (0.20 g, 27%),: TLC $R_f$ (5:1 methylene chloride/ethyl acetate)=0.59; $^1$H NMR (300 MHz, DMSO-$d_6$): δ 10.96 (s, H), 7.63–7.59 (m, 2H), 7.30 (d, J=9.9 Hz, 1H), 6.94–6.84 (m, 0.3H), 6.01 (s, 2H), 5.20 (d, J=9.9 Hz, 1H), 4.19 (q, J=7.3 Hz, 2H), 3.87–3.82 (m, 1H), 3.12–3.03 (m, 1H), 2.89–2.78 (m, 1H), 2.28 (t, J=7.1 Hz, 3H) ppm. The latter eluting trans isomer also was isolated as an orange solid (0.17 g, 23%): TLC $R_f$ (5:1 methylene chloride/ethyl acetate)=0.28; $^1$H NMR (300 MHz, DMSO-$d_6$): δ 11.21 (s, 1H), 7.69 (s, 1H), 7.63 (d, J=9.9 Hz, 1H), 7.30 (d, J=9.9 Hz, 1H), 6.88–6.82 (m, 2H), 6.68 (d, J=9.0 Hz, 1H), 5.98 (s, 2H), 5.31 (s, 1H), 4.12–4.05 (m, 2H), 3.84–3.79 (m, 1H), 3.14–3.03 (dd, J=5.0, 15.0 Hz, 1H), 2.95–2.88 (dd, J=8.0, 150 Hz, 1H), 1.18 (t, J=7.5 Hz, 3H) ppm.

Intermediate 29

Preparation of (+/−)-cis-2-Chloroacetyl-β-Carboline

Chloroacetyl chloride (0.055 mL, 69 mmol) was added to a solution of Intermediate 28 (0.20 g, 0.51 mmol) and triethylamine (0.10 mL, 0.72 mmol) in methylene chloride (10 mL) at 0° C. under an argon blanket, after which the solution was warmed to room temperature over 2 hours. The yellow solution then was diluted with methylene chloride (40 mL), washed with water (20 mL), and saturated $NaHCO_3$ solution (20 mL). The organic layer was dried over $Na_2SO_4$, and the solvent was removed under reduced pressure to afford Intermediate 29 as a yellow oil which was used without further purification: TLC $R_f$ (8:1 methylene chloride/ethyl acetate)=0.76.

EXAMPLE 7

Preparation of (+−, cis)-6-Benzo[1,3]dioxol-5-yl-2-methyl-1,4-dioxo-1,2,3,4,6,7,12,12a-octahydropyrazino[1',2':1,6]pyrido[3,4-b]indole-9-carbonitrile A solution of cis-2-chloroacetyl-β-carboline 7 (0.51 mmol) and methylamine (5.1 mL, 10.2 mmol, 2 M solution in THF) in methanol (9.0 mL) was heated at 50° C. for 16 hours. The resulting solids were isolated by filtration under reduced pressure to provide Example 7 as a pale yellow solid (94 mg. 44%): mp 329–331° C.; TLC $R_f$(5:1:0.5 methylene chloride/ethyl acetate/methanol)=0.50; $^1$H NMR (300 MHz, DMSO-$d_6$): δ 11.65 (s, H), 7.81 (s, 1H), 7.76 (d, J=8.2 Hz, 1H), 7.33 (d, J=8.4 Hz, 1H), 6.88 (s, 1H), 6.79 (s, 2H), 6.17 (s, 2H), 5.93 (s, 2H), 4.43–4.38 (dd, J=4.1, 11.5 Hz, 1H), 4.17 (d, J=17.3 Hz, 1H), 3.95 (d, J=17.3 Hz, 1H), 3.59 (dd, J=4.4, 16.0 Hz, 1H), 3.00 (dd, J=11.5, 15.7 Hz, 1H), 2.93 (s, 3H) ppm; ESI MS m/z 413 $[C_{23}H_{18}N_4O_4$—H$]^+$. Anal. Calcd. for $C_{23}H_{18}N_4O_4$; C, 66.66; H, 4.38; N, 13.52. Found: C, 66.49; H, 4.43; N, 13.30. HPLC analysis (Aquasil C18 Column, 100×4.6 mm, Retention Time=9.74 min; 45:55 0.03% acetonitrile:water/TFA; flow=0.50 mL/min; detector @ 254 nm; temperature ambient) showed one peak, with a purity of 100.0%. The stereochemistry of analog Example 7 was confirmed to be the desired cis isomer by a series of NOE difference experiments: a positive NOE enhancement from the C12a proton at 4.40 ppm to the C6 proton at 6.17 ppm; a positive NOE enhancement from the C6 proton at 6.17 ppm to the C12a proton at 4.40 ppm.

PREPARATION OF EXAMPLE 8

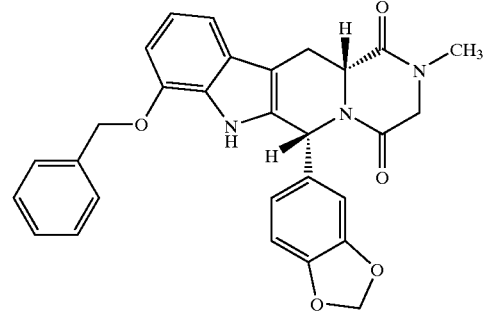

Example 8 was prepared from 3-methyl-2-nitrophenol as depicted in the following synthetic scheme. Intermediate 31 was prepared as disclosed in G. M. Carrera et al., *Synlet*, p. 93 (1994) and M. P. Moyer et al., *J. Org. Chem.*, 51, p. 5106 (1986), and converted to Intermediate 32 as disclosed in Y. Yokohama, *Tetrahedron Lett.*, 40, p. 7803 (1999) and H. R. Snyder et al., *J. Am. Chem. Soc.*, 77, p. 1257 (1955).

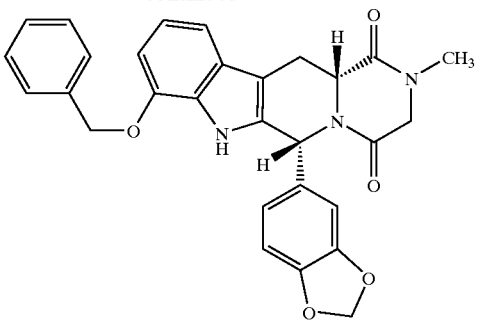

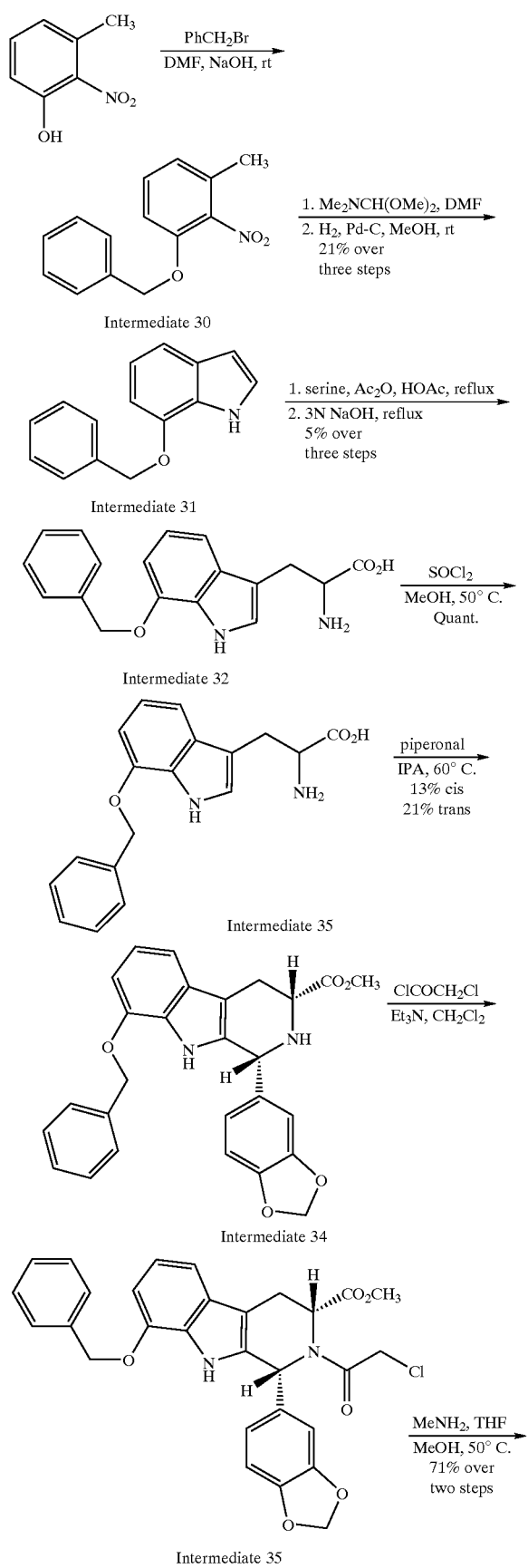

Example 8

Intermediate 31
Preparation of 7-Benzyloxyindole

Benzyl bromide (15.4 ml, 130 mmol) was added dropwise to a solution of 3-methyl-2-nitrophenol (20.0 g, 130 mmol) and sodium hydroxide (6.0 g, 144 mmol) in anhydrous N,N-dimethylformamide (100 mL) at 0° C. under a nitrogen blanket. The resulting red solution was slowly warmed to room temperature, stirring for a total of 17 hours. The mixture then was diluted with ethyl acetate (706 ml), stirred for 15 minutes, and the solids were removed by filtration under reduced pressure. The bright yellow filtrate was concentrated under reduced pressure to provide Intermediate 30 as a dark yellow residue, which was used without further purification (31.8 g): TLC $R_f$ (5:1 hexanes/ethyl acetate)=0.50.

A mixture of Intermediate 30 (31.8 g, 130 mmol), pyrrolidine (11.0 mL, 130 mmol), and N,N-dimethylformamide dimethyl acetal (52 mL, 392 mmol) in anhydrous N,N-dimethylformamide (100 mL) was heated at 110° C. under a nitrogen blanket for 3 hours. The cooled mixture was diluted with water (1.5 L), extracted with ether (2×500 mL), dried over $Na_2SO_4$, and filtered. The solvent was removed under reduced pressure to afford the intermediate enamine as a dark red oil, which was immediately used in the next step without purification.

A solution of the enamine in methanol (150 mL) and acetic acid (5 mL) was treated with a catalytic amount of 10% palladium on carbon (2 g, 10% wet), and the resulting mixture was stirred under a hydrogen atmosphere (50 psi) at room temperature for 2 hours. The palladium catalyst was removed by vacuum filtration through $MgSO_4$ (10 g), and the filtrate was concentrated under reduced pressure to provide a dark brown residue. The residue was purified by flash column chromatography, eluting with ethyl acetate/chloroform (1:19), to provide Intermediate 31 as an off-white solid (3.82 g, 21% over three steps): TLC $R_f$ (4:1 hexanes/ethyl acetate)=0.61; $^1H$ NMR (300 MHz, DMSO-$d_6$): δ 11.18 (s, 1H), 7.56 (d, J=7.2 Hz, 2H), 7.43–7.38 (m, 3H), 7.35 (s, 1H), 7.23 (d, J=2.9 Hz, 1H), 6.88 (t, J=7.6 Hz, 1H), 6.72 (d, J=7.6 Hz, 1H), 6.39 (t, J=2.5 Hz, 1H), 5.26 (s, 2H) ppm.

Intermediate 32
Preparation of (+/−)-7-Benzyloxytryptophan

Acetic anhydride (0.5 mL, 5.2 mmol) was added to a slurry of Intermediate 31 (0.575 g, 2.6 mmol) and DL-serine (0.270 g, 2.6 mmol) in anhydrous acetic acid (5 mL) at room temperature under a nitrogen blanket. The resulting orange solution was heated to reflux and stirred for 24 hours. The cooled mixture then was concentrated under reduced pressure to provide the intermediate N-acetyltryptophan as dark red oil, which was used immediately without purification.

A suspension of the intermediate N-acetyltryptophan in 3 N sodium hydroxide was heated at reflux for 17 hours, then cooled to room temperature. The mixture was diluted with water (50 mL), washed with diethyl ether (50 mL), slurried with charcoal (1 g), and filtered through a plug of silica gel (20 g), eluting with water (100 mL). The filtrate was acidified to pH 4 with 6 N HCl (1 mL), and the solution was filtered through a plug of DOWEX 50×8-100 ion-exchange resin (100 g), eluting with concentrated ammonium hydroxide/methanol (1:3), to provide Intermediate 32 as a gray powder (0.040 g, 5% over two steps): $^1$H NMR (300 MHz, CD$_3$OD): δ 7.51 (d, J=7.0 Hz, 2H), 7.39–7.29 (m, 3H), 7.17 (d, J=7.9 Hz, 1H), 7.04 (s, 1H), 6.91 (t, J=7.6 Hz, 1H), 6.68 (d, J=7.7 Hz, 1H), 5.21 (s, 2H), 4.72–4.68 (m, H), 3.34–3.29 (m, 1H), 3.16–3.09 (m, 1H) ppm.

Intermediate 33

Preparation of (+/−)-7-Benzyloxytryptophan Methyl Ester Hydrochloride

Thionyl chloride (0.4 mL, 4.8 mmol) was added to a suspension of Intermediate 32 (0.600 g, 1.9 mmol) in anhydrous methanol (10 mL) at 0° C. under a nitrogen blanket. The resulting mixture was heated to 50° C. and stirred for 1 hour, then cooled to room temperature. The resulting dark green solution was concentrated under reduced pressure to provide Intermediate 33 as a light green powder which was used without further purification (0.710 g, 100%): TLC R$_f$ (4:1 chloroform/methanol)=0.87; $^1$H NMR (300 MHz, DMSO-d$_6$): δ 11.18 (s, 1H), 8.48 (bs, 2H), 7.55 (d, J=7.2 Hz, 1H), 7.43–7.41 (m, 3H), 7.38 (s, 1H), 7.34 (d, J=7.2 Hz, 1H), 7.10–6.91 (m, 1H), 6.75 (d, J=7.6 Hz, 1H), 5.26 (s, 2H), 4.42 (s, 1H), 3.66 (s, 3H), 3.35–3.26 (m, 2H) ppm.

Intermediate 34

Preparation of (+/−)-cis-β-Carboline

A solution of Intermediate 33 (0.710 g, 2.0 mmol) and piperonal (0.300 g, 2.0 mmol) in anhydrous isopropanol (10 mL) was heated at reflux under a nitrogen blanket for 6 hours. The resulting orange solution was cooled to room temperature, neutralized with saturated NaHCO$_3$ solution (1 mL), then the solvent was removed under reduced pressure to provide brown solid. The residue was purified by flash column chromatography, eluting with chloroform/ethyl acetate (19:1), to provide Intermediate 34 as a colorless oil (0.120 g, 13%): TLC R$_f$(4:1 chloroform/ethyl acetate)=0.57; $^1$H NMR (300 MHz, CDCl$_3$): δ 7.70 (s, 1H), 7.44–7.26 (m, 5H), 7.17 (d, J=7.8 Hz, 1H), 7.04 (t, J=7.7 Hz, 1H), 6.88–6.70 (m, 4H), 5.94 (s, 2H), 5.16 (s, 2H), 3.93 (dd, J=4.1, 11.0 Hz, 1H), 3.81 (s, 3H), 3.22–3.17 (m, 1H), 3.03–2.95 (m, 1H) ppm. The latter eluting trans isomer was also isolated as a colorless oil, but was not characterized (0.190 g, 21%) TLC R$_f$(4:1 chloroform/ethyl acetate)=0.51.

Intermediate 35

Preparation of (+/−)-cis-2-Chloroacetyl-β-carboline

Chloroacetyl chloride (0.03 mL, 0.3 mmol) was added to a solution of Intermediate 34 (0.120 g, 0.3 mmol) and triethylamine (0.05 mL, 0.3 mmol) in methylene chloride (5mL) at 0° C. under an argon blanket, then warmed to room temperature over 1 hour. The solvent then was removed under reduced pressure to yield Intermediate 35 as a yellow powder which was used without further purification: TLC R$_f$ (4:1 chloroform/ethyl acetate)=0.71.

EXAMPLE 8

Preparation of (+−, cis)-6-Benzo[1,3]dioxol-5-yl-8-benzyloxy-2-methyl-2,3,6,7,12,12a-hexahydropyrazino [1'2':1,6]pyrido[3,4-b]indole-1,4-dione A solution of Intermediate 35 (0.3 mmol) and methylamine (0.7 mL, 1.2 mmol, 2 M solution in THF) in methanol (5 mL) was heated at 50° C. for 20 hours. The resulting solids were isolated by filtration under reduced pressure to provide Example 8 as a pale yellow powder (0.092 g, 71% over two steps): mp 150–161° C.; TLC R$_f$(4:1 chloroform/ethyl acetate)=0.19; $^1$H NMR (300 MHz, CDCl$_3$): δ 8.25 (s, H), 7.45–7.34 (m, 6H), 7.26–7.22 (m, 1H), 7.06 (t, J=7.9 Hz, 1H), 6.84 (d, J=8.0 Hz, 1H), 6.74–6.65 (m, 2H), 6.17 (s, 1H), 5.86 (s, 2H), 5.14 (s, 2H), 4.23 (dd, J=4.3, 11.5 Hz, 1H), 3.95 (dd, J=17.4, 52.8 Hz, 2H), 3.75 (dd, J=4.5, 11.4 Hz, 1H), 3.19 (dd, J=4.3, 11.7 Hz, 1H), 3.01 (s, 3H) ppm; ESI MS m/z 496 [C$_{29}$H$_{25}$N$_3$O$_5$+H]$^+$. Anal. Calcd. for C$_{29}$H$_{25}$N$_3$O$_5$: C, 70.29; H, 5.09; N, 8.48. Found: C, 69.71; H, 5.09; N, 8.41. The stereochemistry of Example 8 was confirmed to be the desired cis isomer by a series of NOE difference experiments: a positive NOE enhancement from the C12a proton at 4.23 ppm to the c6 proton at 6.17 ppm; a positive NOE enhancement from the C6 proton at 6.17 ppm to the C12a proton at 4.23 ppm.

The following compounds are additional examples of compounds of structural formula (I) that can be prepared by methods analogous to the preparation of Examples 1 through 8.

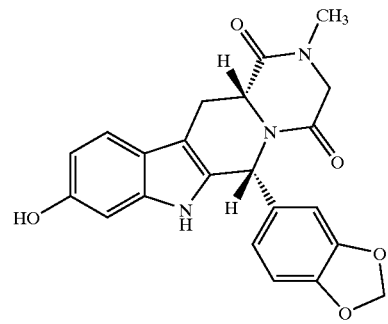

EXAMPLE 9

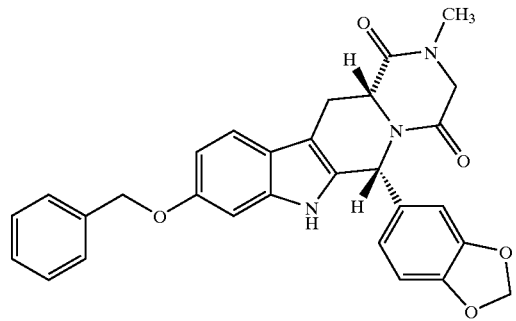

EXAMPLE 10

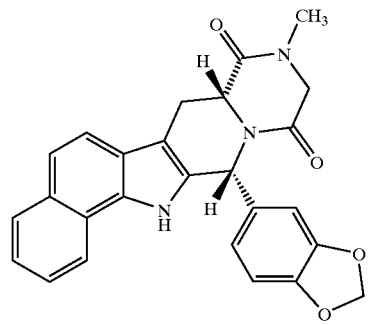

EXAMPLE 11

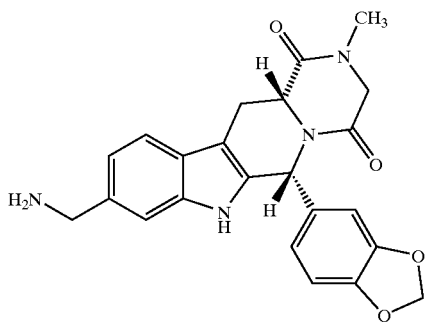

EXAMPLE 12

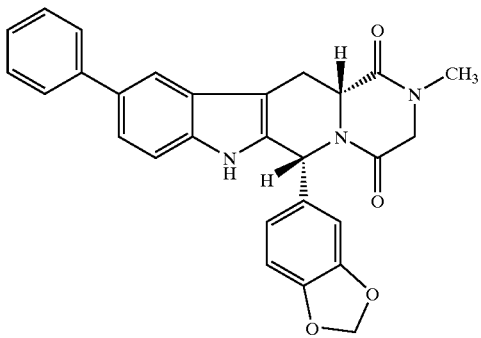

EXAMPLE 13

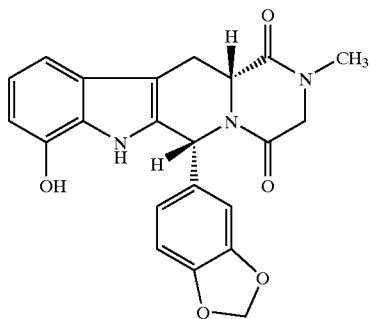

EXAMPLE 14

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 $\mu$M, and preferably less than about 25 $\mu$M, and more preferably less than about 15 $\mu$m. The compounds of the present invention typically exhibit an $IC_{50}$ value against recombinant human PDE5 of less than about 1 $\mu$M, and often less than about 0.05 $\mu$M. To achieve the full advantage of the present invention, a present PDE5 inhibitor has an $IC_{50}$ of about 0.1 nM to about 15 $\mu$M.

The production of recombinant human PDEs and the $IC_{50}$ determinations can be accomplished by well-known methods in the art. Exemplary methods are described as follows:

Expression of Human PDEs

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 $\mu$L reaction mixture containing (final concentrations) 40 mM Tris HCl (pH 8.0), 1 $\mu$M $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) $\mu$g of Crotalus atrox venom then was added, and the incubation was continued for 3 minutes (15 minutes total). The reaction was stopped by addition of 200 $\mu$L of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 $\mu$M $ZnSO_4$). Cells were lysed in a Microfluidizer® (Microfluidics Corp.) using nitrogen at 20,000 psi. The lysate was centrifuged and filtered through 0.45 $\mu$m disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM MgCl$_2$, 0.25 mM DTT, 10 μM ZnSO$_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM MgCl$_2$, 0.25 mM DTT, 10 μM ZnSO$_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 μM ZnSO$_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta,* 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[H$^3$]-cGMP. Unless otherwise indicated, the enzyme used was a human recombinant-PDE5 (ICOS Corp., Bothell, Wash.).

Compounds of the invention were dissolved in DMSO finally present at 2% in the assay. The incubation time was 30 minutes during which the total substrate conversion did not exceed 30%.

The IC$_{50}$ values for the compounds examined were determined from concentration-response curves typically using concentrations ranging from 10 nM to 10 μM. Tests against other PDE enzymes using standard methodology showed that compounds of the invention are selective for the cGMP-specific PDE enzyme.

Biological Data

The compounds according to the present invention were typically found to exhibit an IC$_{50}$ value of less than 500 nM. In vitro test data for representative compounds of the invention is given in the following table:

TABLE 1

In vitro results

| Example | PDE5 IC$_{50}$ (nM) |
|---|---|
| 1 | 48.1 |
| 2 | 401.7 |
| 3 | 1.2 |
| 4 | 6.0 |
| 5 | 288.0 |
| 6 | 151.0 |
| 7 | 7.0 |
| 8 | 37.0 |

Obviously, many modifications and variations of the invention as hereinbefore set forth can be made without departing from the spirit and scope thereof, and, therefore, only such limitations should be imposed as are indicated by the appended claims.

What is claimed is:
1. A compound having a formula

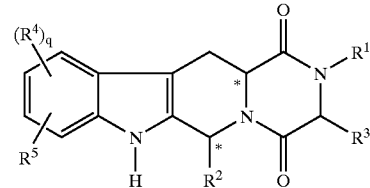

wherein R$^1$ is selected from the group consisting of hydrogen, C$_{1-6}$alkyl, C$_{2-6}$alkenyl, C$_{2-6}$alkynyl, halo-C$_{1-6}$alkyl, C$_{3-8}$cycloalkyl, heteroC$_{3-8}$cycloalkyl, C$_{3-8}$cycloalkylC$_{1-3}$alkyl, arylC$_{1-3}$alkyl, and heteroarylC$_{1-3}$alkyl;

R$^2$ is selected from the group consisting of an optionally substituted monocyclic aromatic ring selected from the group consisting of benzene, thiophene, furan, and pyridine, and an optionally substituted bicyclic ring

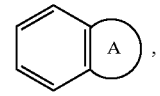

wherein the fused ring A is a 5- or 6-membered ring, saturated or partially or fully unsaturated, and comprises carbon atoms and optionally one or two heteroatoms selected from oxygen, sulfur, and nitrogen;

R$^3$ is selected from the group consisting of hydrogen and C$_{1-6}$alkyl, or R$^1$ and R$^3$ together represent a 3- or 4-membered alkyl or alkenyl chain component of a 5- or 6-membered ring;

R$^4$, independently, is selected from the group consisting of aryl,

Het,

C$_{3-8}$cycloalkyl,

YC$_{3-8}$cycloalkyl (wherein Y is oxygen, sulfur, or NR$^a$),

C(=O)R$^a$,

OC(=O)R$^a$,

C(=O)OR$^a$,

C$_{1-4}$alkyleneNR$^a$R$^b$,

C$_{1-4}$alkyleneHet,

C$_{1-4}$alkyleneC(=O)OR$^a$,

C(=O)NR$^a$SO$_2$R$^c$,

C(=O)C$_{1-4}$alkyleneHet,

C(=O)NR$^a$R$^b$,

C(=O)NR$^a$R$^c$,

C(=O)NR$^a$C$_{1-4}$alkyleneOR$^b$,

C(=O)NR$^a$C$_{1-4}$alkyleneHet,

OR$^a$,

OC$_{1-4}$alkyleneC(=O)OR$^a$,

OC$_{2-4}$alkyleneNR$^a$R$^b$,

OC$_{1-4}$alkyleneHet,

OC$_{2-4}$alkyleneOR$^a$,

OC$_{1-4}$alkyleneNR$^a$C(=O)OR$^b$,

NR$^a$R$^b$,

NR$^a$C$_{1-4}$alkyleneNR$^a$R$^b$,

NR$^a$C(=O)R$^b$,
NR$^a$C(=O)NR$^a$R$^b$,
N(SO$_2$C$_{1-4}$alkyl)$_2$,
NR$^a$(SO$_2$C$_{1-4}$alkyl),
nitro (NO$_2$),
trifluoromethyl,
trifluoromethoxy,
cyano (CN),
SO$_2$NR$^a$R$^b$,
SO$_2$R$^a$,
SOR$^a$,
SR$^a$,
and OSO$_2$CF$_3$;

R$^5$ is selected from the group consisting of hydrogen, halogen, and C$_{1-6}$alkyl;

or R$^4$ and R$^5$ are taken together with the carbon atoms to which they are attached to form a 5-, 6-, or 7-membered ring, saturated or partially or fully unsaturated, optionally substituted and optionally containing one or two heteroatoms selected from the group consisting of oxygen, sulfur, and nitrogen;

R$^a$ is selected from the group consisting of hydrogen, C$_{1-6}$alkyl, C$_{3-8}$cycloalkyl, aryl, arylC$_{1-3}$-alkyl, C$_{1-3}$alkylenearyl, and Het;

R$^b$ is selected from the group consisting of hydrogen, C$_{1-6}$alkyl, aryl, arylC$_{1-3}$alkyl, C$_{1-3}$alkylenearyl, and Het;

R$^c$ is phenyl or C$_{4-6}$cycloalkyl, either optionally substituted with one or more substituent selected from the group consisting of halo, C(=O)OR$^a$, and OR$^a$;

Het is a 5- or 6-membered heterocyclic group, saturated or partially or fully unsaturated, containing at least one heteroatom selected from the group consisting of oxygen, nitrogen, and sulfur, and optionally substituted with C$_{1-4}$alkyl or C(=O)OR$^b$;

q is 1, 2, or 3; and pharmaceutically acceptable salts and hydrates thereof.

2. The compound of claim 1 represented by the formula

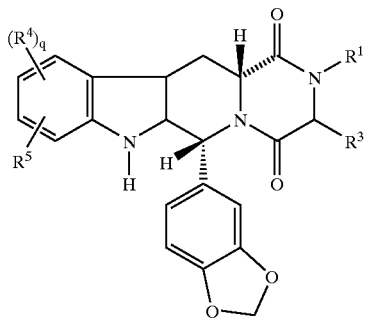

and pharmaceutically acceptable salts and solvates thereof.

3. The compound of claim 1 wherein R$^1$ is selected from the group consisting of hydrogen, C$_{1-4}$alkyl, haloC$_{1-4}$alkyl, C$_{3-6}$cycloalkyl, and C$_{3-6}$cycloalkylmethyl.

4. The compound of claim 1 wherein R$^3$ is hydrogen.

5. The compound of claim 1 wherein R$^2$ is an optionally substituted bicyclic ring selected from the group consisting of naphthalene, indene, benzoxazole, benzothiazole, benzisoxazole, benzimidazole, quinoline, indole, benzothiophene, and benzofuran.

6. The compound of claim 1 wherein R$^2$ is

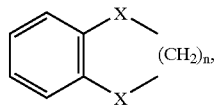

and wherein n is an integer 1 or 2, and X, independently, are C(R$^a$)$_2$, O, S, or NR$^a$.

7. The compound of claim 1 wherein R$^2$, substituted or unsubstituted, is selected from the group consisting of

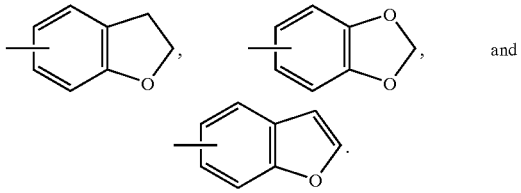

8. The compound of claim 7 wherein R$^2$ is substituted with a substituent selected from the group consisting of halogen, C$_{1-3}$alkyl, OR$^a$, CO$_2$R$^a$, halomethyl, halomethoxy, cyano, nitro, and NR$^a$R$^b$.

9. The compound of claim 1 wherein R$^4$ is selected from the group consisting of aryl, trifluoromethyl, trifluoromethoxy, C(=O)R$^a$, C(=O)OR$^a$, C(=O)NR$^a$R$^b$, C(=O)NR$^a$R$^c$, OR$^a$, CN, C$_{1-4}$alkyleneNR$^a$R$^b$, OC$_{2-4}$alkyleneNR$^a$R$^b$, SO$_2$NR$^a$R$^b$, OC(=O)R$^a$, NR$^a$R$^b$, Het, C$_{3-8}$-cycloalkyl, and YC$_{3-8}$cycloalkyl.

10. The compound of claim 9 wherein R$^4$ is selected from the group consisting of CH$_2$NR$^a$R$^b$, aryl, CN, OR$^a$, C(=O)OR$^a$, and NR$^a$R$^b$.

11. The compound of claim 10 wherein R$^4$ is selected from the group consisting of CH$_2$NH$_2$, CO$_2$H, CO$_2$CH$_3$, C$_6$H$_5$, OCH$_2$C$_6$H$_5$, OH, CN, and OCH$_3$.

12. The compound of claim 1 wherein R$^4$ and R$^5$ are taken together to form a 6-membered saturated or unsaturated ring, optionally substituted and optionally containing one or two heteroatoms.

13. The compound of claim 12 wherein R$^4$ and R$^5$ are taken together to form a phenyl ring.

14. The compound of claim 1 wherein R$^5$ is hydrogen.

15. A compound selected from the group consisting of

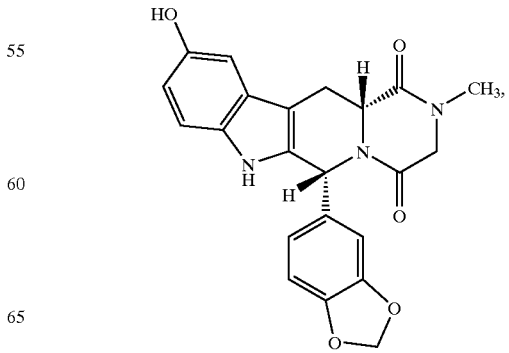

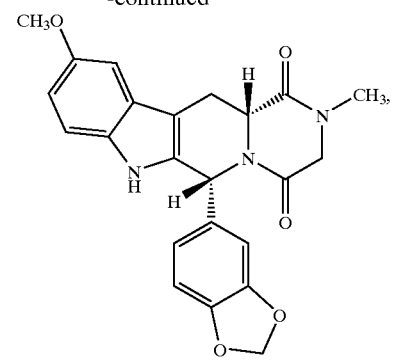
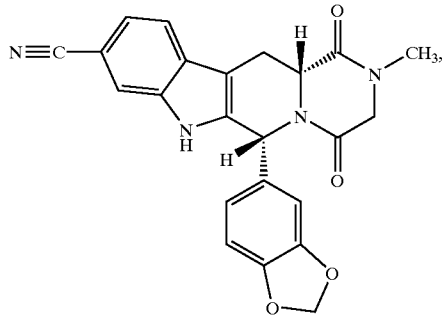
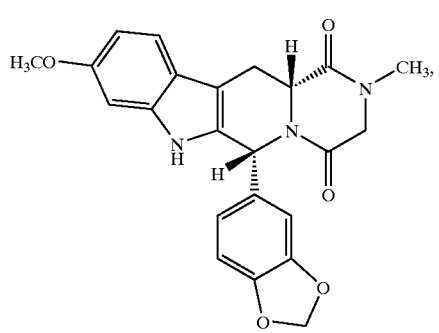
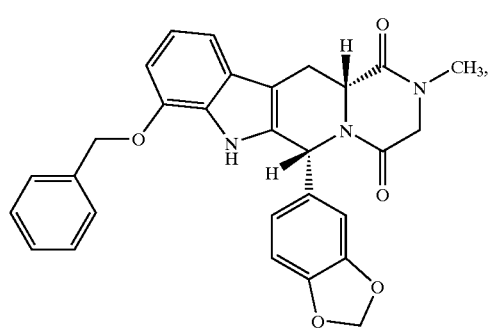
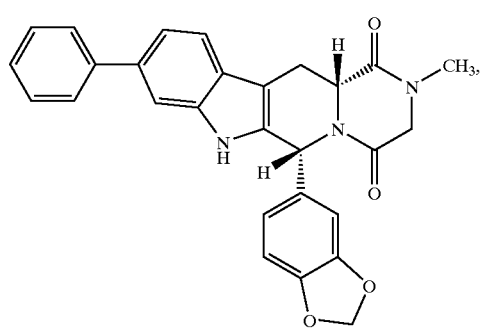
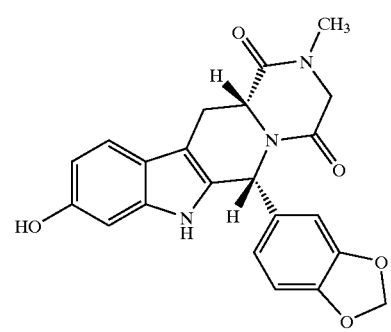
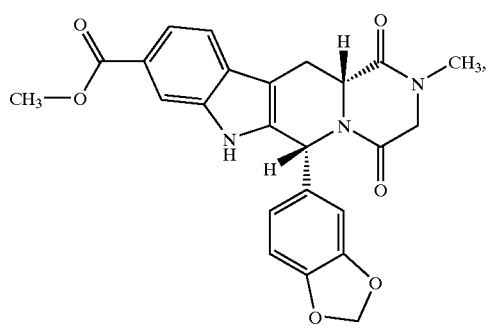
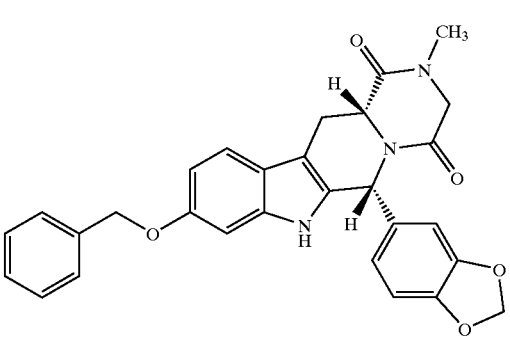
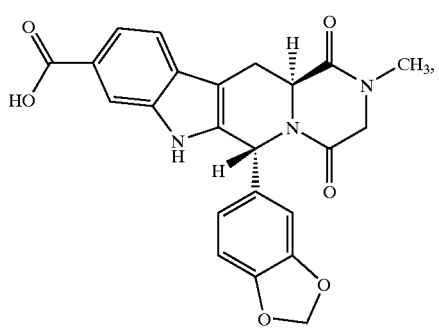
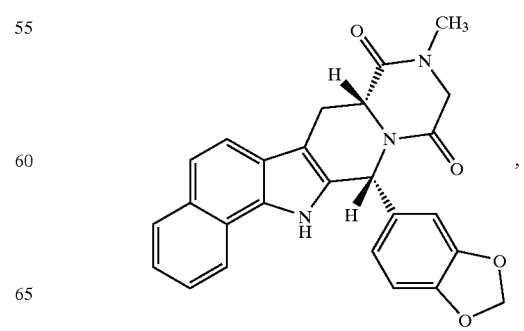

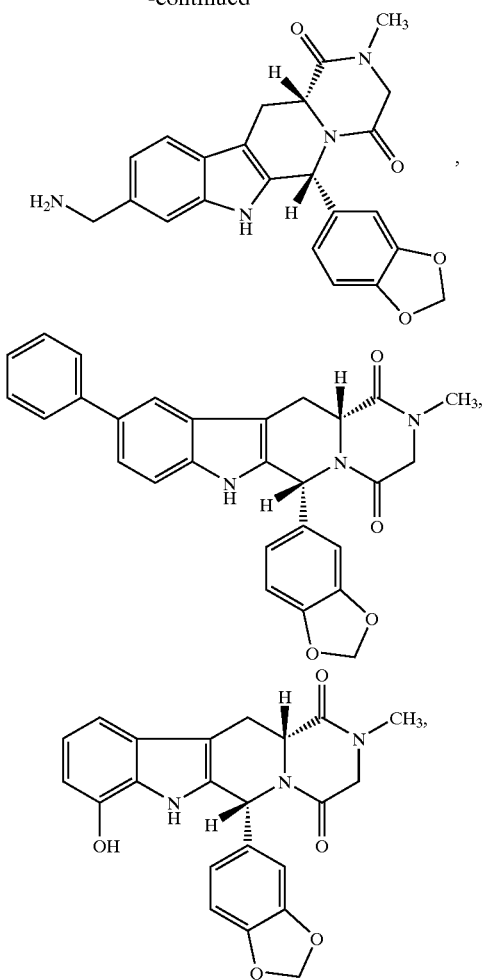

and pharmaceutically acceptable salts and solvates thereof.

16. A pharmaceutical composition comprising a compound of claim 1, together with a pharmaceutically acceptable diluent or carrier.

17. A method of treating a male animal in the treatment of male erectile dysfunction comprising treating said male animal with an effective amount of a pharmaceutical composition comprising a compound of claim 1, together with a pharmaceutically acceptable diluent or carrier.

18. The method of claim 17 wherein the treatment is an oral treatment.

19. A method of treating a male or female animal in the treatment of a condition where inhibition of a cGMP-specific PDE is of a therapeutic benefit comprising treating said animal with an effective amount of a pharmaceutical composition comprising a compound of claim 1, together with a pharmaceutically acceptable diluent or carrier, wherein the condition is selected from the group consisting of stable angina, unstable angina, variant angina, hypertension, pulmonary hypertension, chronic obstructive pulmonary disease, malignant hypertension, pheochromocytoma, acute respiratory distress syndrome, congestive heart failure, acute renal failure, chronic renal failure, atherosclerosis, a condition of reduced blood vessel patency, a peripheral vascular disease, a vascular disorder, thrombocythemia, myocardial infarction, bronchitis, chronic asthma, allergic asthma, allergic rhinitis, glaucoma, peptic ulcer, a gut motility disorder, postpercutaneous transluminal coronary angioplasty, carotid angioplasty, post-bypass surgery graft stenosis, osteoporosis, preterm labor, benign prostatic hypertrophy, and irritable bowel syndrome.

20. A method of treating a female animal in the treatment of female sexual arousal disorder comprising treating said female animal with an effective amount of a pharmaceutical composition comprising a compound of claim 1, together with a pharmaceutically acceptable diluent or carrier.

21. The method of claim 20 wherein the treatment is an oral treatment.

\* \* \* \* \*

UNITED STATES PATENT AND TRADEMARK OFFICE
CERTIFICATE OF CORRECTION

PATENT NO.    : 6,872,721 B2
DATED         : March 29, 2005
INVENTOR(S)   : Orme et al.

It is certified that error appears in the above-identified patent and that said Letters Patent is hereby corrected as shown below:

Title page, Item [54] and Column 1, lines 1 and 3,
Title, "12A-" should be -- 12a- -- and "[3,4B]" should be -- [3,4b] --

Column 3,
Line 48, "pyrinidinyl," should be -- pyrimidinyl --

Column 9,
Line 58, "injected-" should be -- injected --

Column 14,
Line 49, ":1,6)" should be -- :1,6] --

Column 16,
Line 66, "(S," (both occurrences) should be -- (s, --

Column 17,
Lines 50-60, " 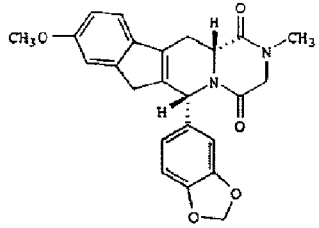 " should be -- 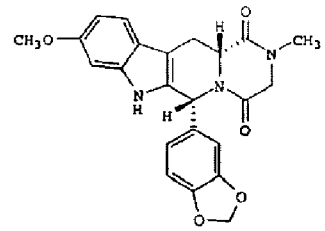 --

Line 66, "Col," should be -- Co., --

Column 22,
Line 53, "darkred" should be -- dark red --

Column 24,
Line 65, "A$_2$O, AcOH" should be -- Ac$_2$O, AcOH --

Column 27,
Line 6, "5-Carboline" should be -- β-Carboline --

UNITED STATES PATENT AND TRADEMARK OFFICE
CERTIFICATE OF CORRECTION

PATENT NO. : 6,872,721 B2
DATED : March 29, 2005
INVENTOR(S) : Orme et al.

It is certified that error appears in the above-identified patent and that said Letters Patent is hereby corrected as shown below:

Column 31,
Line 47, "(10.0 mL)," should be -- (100 mL), --
Line 56, "(m, 0.3H)," should be -- (m, 3H), --
Line 58, "2.28" should be -- 1.28 --
Line 66, "150 Hz," should be -- 15.0 Hz, --

Column 33,
Line 10, "1. Me$_2$NCH(OMe)$_2$, DMF" should be -- 1. Me$_2$NCH(OMe)$_2$, DMF pyrrolidine, 110°C --

Column 35,
Line 13, "(m, H)," should be -- (m, 1H), --
Line 56, "(5mL)" should be -- (5 mL) --

Column 37,
Line 1, "EXAMPLE 11" should appear under the last chemical structure at the bottom of column 36

Column 39,
Line 30, "recombinant-PDE5" should be -- recombinant PDE5 --

Signed and Sealed this

Twenty-eighth Day of June, 2005

JON W. DUDAS
*Director of the United States Patent and Trademark Office*